US011915802B2

(12) United States Patent
Redinger et al.

(10) Patent No.: US 11,915,802 B2
(45) Date of Patent: Feb. 27, 2024

(54) ACCELERATED PROCESSING OF GENOMIC DATA AND STREAMLINED VISUALIZATION OF GENOMIC INSIGHTS

(71) Applicant: SHARECARE AI, INC., Palo Alto, CA (US)

(72) Inventors: Brett Robert Redinger, Oakland, CA (US); Kartik Thakore, Palo Alto, CA (US); Sandra Ann R Steyaert, Izegem (BE); Walter Adolf De Brouwer, Los Altos, CA (US); Srivatsa Akshay Sharma, Palo Alto, CA (US); Lijing Guo, San Francisco, CA (US)

(73) Assignee: SHARECARE AI, INC., Palo Alto, CA (US)

( * ) Notice: Subject to any disclaimer, the term of this patent is extended or adjusted under 35 U.S.C. 154(b) by 0 days.

(21) Appl. No.: 16/985,183

(22) Filed: Aug. 4, 2020

(65) Prior Publication Data
US 2021/0043285 A1 Feb. 11, 2021

Related U.S. Application Data

(60) Provisional application No. 62/883,070, filed on Aug. 5, 2019.

(51) Int. Cl.
*G16H 10/40* (2018.01)
*G06F 16/27* (2019.01)
(Continued)

(52) U.S. Cl.
CPC ............. *G16H 10/40* (2018.01); *G06F 9/451* (2018.02); *G06F 9/4881* (2013.01);
(Continued)

(58) Field of Classification Search
None
See application file for complete search history.

(56) References Cited

U.S. PATENT DOCUMENTS 5,920,644 A 7/1999 Fujimoto et al.
8,275,175 B2 9/2012 Baltatu et al.
(Continued)

FOREIGN PATENT DOCUMENTS

EP 2854059 A2 4/2015

OTHER PUBLICATIONS

U.S. Appl. No. 15/946,629—Office Action dated May 20, 2020, 10 pages.
(Continued)

*Primary Examiner* — Tuankhanh D Phan
(74) *Attorney, Agent, or Firm* — HAYNES BEFFEL & WOLFELD LLP; Ernest John Beffel, Jr.; Korbin S Van Dyke

(57) ABSTRACT

The technology disclosed relates to efficient tertiary analysis of genomic data. The technology disclosed includes splitting a genomic data file into a plurality of segments, and storing segments in the plurality of segments across nodes of a distributed storage system, pushing the segments from the nodes of the distributed storage system to nodes of a distributed, in-memory computing engine, distributing directives of tertiary analysis job contexts for the genomic data file across the nodes of the distributed, in-memory computing engine, directly executing the distributed directives on the segments stored on the nodes of the distributed, in-memory computing engine to cause parallel processing of the segments, and aggregating results of the parallel processing across the nodes of the distributed, in-memory computing engine to produce an output.

15 Claims, 23 Drawing Sheets
(17 of 23 Drawing Sheet(s) Filed in Color)

Poly-omics Pipeline 1500

(51) Int. Cl.
G16H 70/60 (2018.01)
G06F 9/451 (2018.01)
G16B 45/00 (2019.01)
G16B 50/30 (2019.01)
G06F 16/13 (2019.01)
G06F 9/50 (2006.01)
G06F 9/48 (2006.01)

(52) U.S. Cl.
CPC .......... *G06F 9/5027* (2013.01); *G06F 9/5061* (2013.01); *G06F 16/134* (2019.01); *G06F 16/27* (2019.01); *G16B 45/00* (2019.02); *G16B 50/30* (2019.02); *G16H 70/60* (2018.01); *G06F 9/5066* (2013.01); *G06F 9/5072* (2013.01)

(56) References Cited

U.S. PATENT DOCUMENTS

| | | | |
|---|---|---|---|
| 8,543,428 | B1 | 9/2013 | Jones, III et al. |
| 9,147,133 | B2 | 9/2015 | Fujimura |
| 9,839,376 | B1 | 12/2017 | Ross et al. |
| 10,938,852 | B1 | 3/2021 | Streit |
| 11,177,960 | B2 | 11/2021 | Sly et al. |
| 2006/0206724 | A1 | 9/2006 | Schaufele et al. |
| 2011/0172499 | A1 | 7/2011 | Simons-Nikolova et al. |
| 2011/0291834 | A1 | 12/2011 | Boldyrev et al. |
| 2012/0162404 | A1 | 6/2012 | Howell et al. |
| 2013/0046761 | A1 | 2/2013 | Soderberg et al. |
| 2013/0266195 | A1 | 10/2013 | Shiell et al. |
| 2014/0115515 | A1 | 4/2014 | Adams et al. |
| 2015/0178590 | A1 | 6/2015 | Noma et al. |
| 2015/0213207 | A1 | 7/2015 | Amarasingham et al. |
| 2015/0254890 | A1 | 9/2015 | Noma et al. |
| 2015/0324686 | A1 | 11/2015 | Julian et al. |
| 2015/0339523 | A1 | 11/2015 | Tsunematsu |
| 2015/0363709 | A1 | 12/2015 | Kamei et al. |
| 2016/0253549 | A1 | 9/2016 | Ramic |
| 2016/0306922 | A1* | 10/2016 | van Rooyen .......... G16B 50/30 |
| 2016/0328253 | A1 | 11/2016 | Majumdar |
| 2017/0011280 | A1 | 1/2017 | Soldevila et al. |
| 2017/0206691 | A1 | 7/2017 | Harrises et al. |
| 2018/0289334 | A1 | 10/2018 | De Brouwer et al. |
| 2019/0082211 | A1 | 3/2019 | Vats |
| 2019/0244108 | A1 | 8/2019 | Meyerson et al. |
| 2019/0319977 | A1 | 10/2019 | Gottschlich et al. |
| 2019/0354846 | A1 | 11/2019 | Mellempudi et al. |
| 2020/0082062 | A1 | 3/2020 | Mequanint et al. |
| 2020/0221191 | A1 | 7/2020 | Baughman et al. |
| 2021/0141896 | A1 | 5/2021 | Streit |
| 2021/0326422 | A1 | 10/2021 | Sly et al. |
| 2021/0326433 | A1 | 10/2021 | Sly et al. |
| 2021/0328801 | A1 | 10/2021 | Sly et al. |

OTHER PUBLICATIONS

Kocabey, Enes, et al., "Face to BMI Using Computer Vision to Infer Body Mass Index on Social Media", 2017, 4 pages.
U.S. Appl. No. 15/946,629—Response to Office Action dated May 20, 2020, filed Aug. 20, 2020, 13 pages.
U.S. Appl. No. 15/946,629—Office Action dated Oct. 23, 2020, 9 pages.
U.S. Appl. No. 15/946,629—Notice of Allowance dated Jan. 22, 2021, 16 pages.
U.S. Appl. No. 16/802,485—Notice of Allowance dated Feb. 18, 2021, 10 pages.
Wen, Lingyun, et. al., "A computational approach to body mass index prediction from face images", Feb. 9, 2013, 9 pages.
Parkhi, Omkar M., et. al., "Deep Face Recognition", 2015, 12 pages.
Parkhi, Omkar M., et. al., Visual Geometry Group, 4 pages, [Retrived on Apr. 18, 2021], Retrieved from the Internet < URL: https://www.robots.ox.ac.uk/~vgg/software/vgg_face/>.
Wikipedia, "Diffie-Hellman key exchange", 12 pages [Retrived on Apr. 18, 2021], Retrieved from the Internet < URL: https://en.wikipedia.org/wiki/Diffie-Hellman_key_exchange>.
Whatis.com, "What is Diffie-Hellman Key Exchange?", Mar. 2019, 5 pages, [Retrived on Apr. 18, 2021], Retrieved from the Internet < URL: https://searchsecurity.techtarget.com/definition/Diffie-Hellman-key-exchange>.
Kallam, Sivanagaswathi, "Diffie-Hellman:Key Exchange and Public Key Cryptosystems", Sep. 30, 2015, 27 pages.
Xie, Renjie et al., "A Deep Information-theoretic Framework for Robust Biometric Recognition", Feb. 23, 2019, 7 pages.
U.S. Appl. No. 17/235,871—Office Action dated Jun. 24, 2021, 8 pages.
"Diffie-Hellman Key Exchange", 1 page, [Retrived on Mar. 18, 2021], Retrieved from the Internet < URL: https://i.stack.imgur.com/AEx0X.png>.
Abozaid Anter et al,"Multimodal biometric scheme for human authentication technique based on voice and face recognition fusion", Multimedia Tools and Applications, Kluwer Academic Publishers, Boston, US, vol. 78, No. 12, Dec. 15, 2018 (Dec. 15, 2018), pages.
Suwon Shon et al,"Noise-tolerant Audio-visual Online Person Verification using an Attention-based Neural Network Fusion", arxiv.org, Cornell University Library, 201 Olin Library Cornell University Ithaca, NY 14853, Nov. 27, 2018 (Nov. 27, 2018).
Marras Mirko et al, "Deep Multi-biometric Fusion for Audio-Visual User Re-Identification and Verification", Jan. 25, 2020 (Jan. 25, 2020), Advances in Intelligent Data Analysis XIX; [Lecture Notes in Computer Science; Lect Notes Computer], Springer International Publishing, Cham, pp. 136-157.
Oloyede Muhtahi R O. et al,"Unimodal and Multimodal Biometric Sensing Systems—A Review", IEEE Access, vol. 4, Sep. 16, 2016 (Sep. 16, 2016), pp. 7532-7555.
PCT/US2021/028470 Partial Search Report dated Jul. 23, 2021, 12 pages.
PCT/US2020/045018—International Search Report and Written Opinion dated Dec. 14, 2020, 17 pages.
PCT/US2020/062906—International Search Report and Written Opinion dated Apr. 8, 2021, 10 pages.
Bertoldi et al, "QueryOR: a comprehensive web platform for genetic variant analysis and prioritization", BMC Bioinformatics, Biomed Central Ltd., London, UK, vol. 18, No. 1, Apr. 28, 2017, pp. 1-11, XP021244576, DOI: 10.1186/S12859-017-1654-4.
FIUME—"System for Interpretation of Personal Genomes," Jan. 1, 2015, XP055494359, ISBN: 978-1-339-35927-4, retrieved from the Internet: URL: https://tspace.library.utoronto.ca/bitstream/1807/69278/3/Fiume_Marc-201506_PhD_thesis.pdf, 159 pages.
U.S. Appl. No. 17/235,889—Notice of Allowance dated Jul. 12, 2021, 3 pages.
U.S. Appl. No. 17/235,889—Notice of Allowance dated Jul. 7, 2021, 28 pages.
U.S. Appl. No. 17/235,876—Office Action dated Sep. 9, 2021, 25 pagesa.
Bonawitz et al., Towards Federated Learning at Scale: System Design, Proceedings of the 2nd SysML Conference, dated Mar. 22, 2019, 15 pages.
Thakore, Spark Accelerated Genomics Processing, doc.ai, dated May 7, 2019, 17 pages.
PCT/US2020/022200 International Preliminary Report on Patentability, dated Sep. 23, 2021, 10 pages.
McMahan et. al., Communication-Efficient Learning of Deep Networks from Decentralized Data, Proceedings of the 20th International Conference on Artificial Intelligence and Statistics (AISTATS) 2017, dated Feb. 28, 2017, 11 pages.
U.S. Appl. No. 17/235,871—Response to Office Action dated Jun. 24, 2021, filed Sep. 23, 2021, 10 pages.
U.S. Appl. No. 17/235,871—Notice of Allowance, dated Oct. 5, 2021, 5 pages.
U.S. Appl. No. 17/235,876—Response to Office Action dated Sep. 9, 2021, filed Dec. 8, 2021, 9 pages.
PCT/US2021/028470 International Search Report and Written Opinion, dated Sep. 13, 2021, 17 pages.
U.S. Appl. No. 16/802,485—Notice of Allowance dated Jun. 2, 2021, 10 pages.

(56) References Cited

OTHER PUBLICATIONS

U.S. Appl. No. 17/235,876 Notice of Allowance, dated Jan. 12, 2022, 18 pages.

* cited by examiner

Accelerated Processing Pipeline 100

Doc.ai - VCF to Dataframe

```
val PARQUET_FILE_NAME = INPUT_FILE.stripSuffix(".txt") + ".parquet"

val schema = StructType(
    List(
        StructField("rsid", StringType, false),
        StructField("chromosome", StringType, false),
        StructField("position", IntegerType, false),
        StructField("genotype", StringType, false)
    )
)

val sc_file = sc.textFile(INPUT_FILE)
val rdd = sc_file.filter(line => !line.startsWith("#")).map(line => line.split("\t")).map(entries
=> Row(entries(0), entries(1), entries(2).toInt, entries(3)))
val df = spark.createDataFrame(rdd, schema)

val updated_df = df.withColumn("genotype", when(col("genotype").equalTo("--"),
"..").otherwise(col("genotype"))).sort(asc("chromosome"), asc("position"))
```

FIGURE 4

Doc.ai - Reference Mapping

```
// A reference data is used that can help mapp ancestry to an individuals SNPs reids val df = spark.read.parquet("doc_ai_ancestry_frequencies_50_hgdp_pca_filtered_v3.parquet").createTempView("ANCESTRY_FREQS")

// A SNPs hashing look up table is used to prepare the users' snps to join with ANCESTRY_FREQS val ancestryDF = spark.sql(" select population_freq, snps, ... from (JOINED_USER_POPULATION_DF)

// Finally results are verified by a suite of assertions to detect potential issues
```

FIGURE 5

Search Interface 600

Insights Interface 700

Susceptibility Rating Interface 800

Studies and Publications Interface 1000

Trials Interface 1100

Invite Interface 1600

Image Sequence Interface 1700

Share Interface 1800

Disease Auto-Suggest Interface 2000

ACCELERATED PROCESSING OF GENOMIC DATA AND STREAMLINED VISUALIZATION OF GENOMIC INSIGHTS

PRIORITY DATA

This application claims the benefit of U.S. Patent Application No. 62/883,070, entitled "ACCELERATED PROCESSING OF GENOMIC DATA AND STREAMLINED VISUALIZATION OF GENOMIC INSIGHTS", filed Aug. 5, 2019. The provisional application is incorporated by reference for all purposes.

INCORPORATIONS

The following materials are incorporated by reference as if fully set forth herein: U.S. Patent Application No. 62/734,840, entitled "HASH-BASED EFFICIENT COMPARISON OF SEQUENCING RESULTS", filed Sep. 21, 2018;

U.S. Patent Application No. 62/734,872, entitled "BIN-SPECIFIC AND HASH-BASED EFFICIENT COMPARISON OF SEQUENCING RESULTS", filed Sep. 21, 2018;

U.S. Patent Application No. 62/734,895, entitled "ORDINAL POSITION-SPECIFIC AND HASH-BASED EFFICIENT COMPARISON OF SEQUENCING RESULTS", filed Sep. 21, 2018;

U.S. patent application Ser. No. 16/575,276, entitled "HASH-BASED EFFICIENT COMPARISON OF SEQUENCING RESULTS", filed Sep. 18, 2019;

U.S. patent application Ser. No. 16/575,277, entitled "BIN-SPECIFIC AND HASH-BASED EFFICIENT COMPARISON OF SEQUENCING RESULTS", filed Sep. 18, 2019;

U.S. patent application Ser. No. 16/575,278, entitled "ORDINAL POSITION-SPECIFIC AND HASH-BASED EFFICIENT COMPARISON OF SEQUENCING RESULTS", filed Sep. 18, 2019;

U.S. Patent Application No. 62/942,644, entitled "SYSTEMS AND METHODS OF TRAINING PROCESSING ENGINES", filed Dec. 2, 2019;

U.S. Patent Application No. 62/964,586, entitled "SYSTEM AND METHOD WITH FEDERATED LEARNING MODEL FOR MEDICAL RESEARCH APPLICATIONS", filed Jan. 22, 2020;

U.S. Patent Application No. 62/975,177, entitled "ARTIFICIAL INTELLIGENCE-BASED DRUG ADHERENCE MANAGEMENT AND PHARMACOVIGILANCE", filed Feb. 11, 2020;

U.S. Patent Application No. 62/481,691, entitled "IMAGE-BASED SYSTEM AND METHOD FOR PREDICTING PHYSIOLOGICAL PARAMETERS", filed Apr. 5, 2017;

U.S. patent application Ser. No. 15/946,629, entitled "IMAGE-BASED SYSTEM AND METHOD FOR PREDICTING PHYSIOLOGICAL PARAMETERS", filed Apr. 5, 2018;

U.S. Patent Application No. 62/810,549, entitled "SYSTEM AND METHOD FOR REMOTE MEDICAL INFORMATION EXCHANGE", filed Feb. 26, 2019;

U.S. patent application Ser. No. 16/802,485, entitled "SYSTEM AND METHOD FOR REMOTE MEDICAL INFORMATION EXCHANGE", filed Feb. 26, 2020;

U.S. Patent Application No. 62/816,880, entitled "SYSTEM AND METHOD WITH FEDERATED LEARNING MODEL FOR MEDICAL RESEARCH APPLICATIONS", filed Mar. 11, 2019;

U.S. patent application Ser. No. 16/816,153, entitled "SYSTEM AND METHOD WITH FEDERATED LEARNING MODEL FOR MEDICAL RESEARCH APPLICATIONS", filed Mar. 11, 2020;

U.S. Patent Application No.: PCT/US2020/22200, entitled "SYSTEM AND METHOD WITH FEDERATED LEARNING MODEL FOR MEDICAL RESEARCH APPLICATIONS", filed Mar. 11, 2020;

U.S. Patent Application No. 62/839,151, entitled "SYSTEM AND METHOD FOR INFORMATION EXCHANGE WITH A MIRROR", filed Apr. 26, 2019;

U.S. patent application Ser. No. 16/858,535, entitled "SYSTEM AND METHOD FOR INFORMATION EXCHANGE WITH A MIRROR", filed Apr. 24, 2020;

U.S. Patent Application No. 63/013,536, entitled "ARTIFICIAL INTELLIGENCE-BASED GENERATION OF ANTHROPOMORPHIC SIGNATURES AND USE THEREOF", filed Apr. 21, 2020;

U.S. Patent Application No. 63/023,854, entitled "PRIVACY INTERFACE FOR DATA LOSS PREVENTION VIA ARTIFICIAL INTELLIGENCE MODELS", filed May 12, 2020; and U.S. Patent Application No. 62/883,639, entitled "FEDERATED CLOUD LEARNING SYSTEM AND METHOD", filed Aug. 6, 2019.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Federated Cloud Learning is a distributed machine learning approach which enables model training on a large corpus of secure data that resides in one or more clouds to which the party training the model does not have access to. By applying the right balance of privacy and security techniques it is possible to keep the data secure on the cloud, with minimal leakage of the data itself in the trained model.

The world is becoming increasingly data-driven. Machine learning is driving more automation into businesses, allowing the delivery of new levels of efficiency and products that are tailored to business outcomes and individual customer preferences. This results in dramatically accelerated volumes of data generation.

The global datasphere, defined by International Data Corporation ("IDC") as the summation of all the world's data, whether it is created, captured, or replicated, is predicted to grow from 33 Zettabytes (ZB) in 2018 to 175 ZB by 2025.

Reliance on cloud services for both enterprises and consumers continues to increase. Companies continue to pursue the cloud for data processing needs, and cloud data centers are quickly becoming the new enterprise data repositories. IDC expects that by 2021, there will be more data stored in the cloud than in traditional data centers.

For example, accounts and transactional data is one of the most valuable assets for a large bank. The lending and other product data generated over millions of users, both individual and corporate, over decades, and well-curated, is a rich knowledge graph of information that is valuable for many players in the finance industry. Having access to this data by a private equity fund or a hedge fund will help build or enhance investment models.

Yet today, significant amounts of such data remain predominantly inaccessible to derive valuable insights via machine learning due to privacy and security concerns, as well as regulatory limitations, for example in accordance with General Data Protection Regulation (EU GDPR) and similar regulations in other jurisdictions. There are also concerns about the difficulty to move big data around, de-identifying the data, structuring the process as continuous data-sale vs one-time sale, as well as reputational risks. Such concerns exist widely across any industry and are only becoming more pronounced with the advancement of Big Data.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 4 shows one implementation of converting a VCF file into a DataFrame.

FIG. 5 shows one implementation of performing a join operation on a Parquet-style reference dataset.

DETAILED DESCRIPTION

Accelerated Processing of Genomic Data

Figure 1:
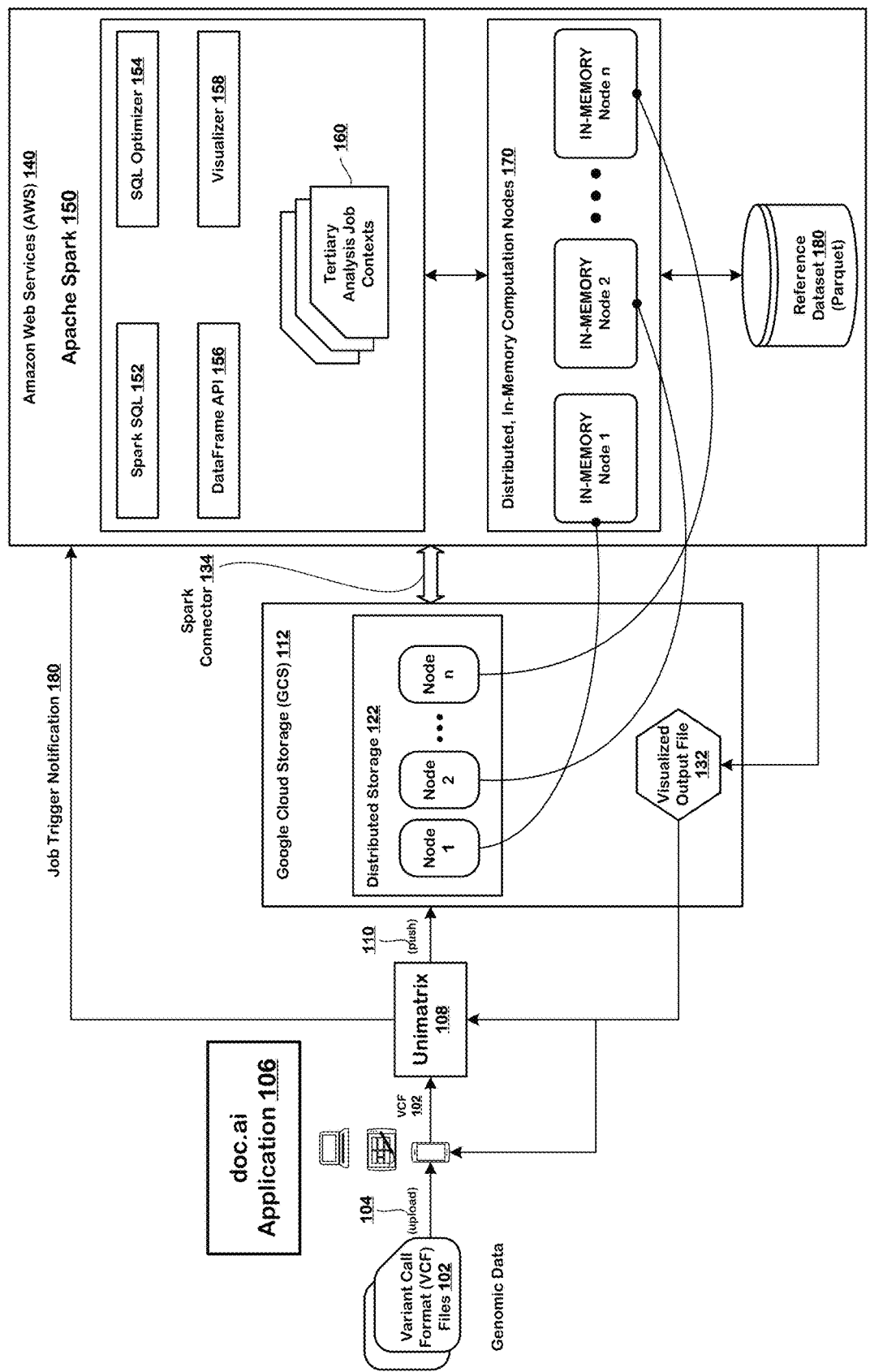
FIG. 1 depicts an accelerated processing pipeline for tertiary analysis of genomic data.

FIG. 1 shows an accelerated processing pipeline 100 for tertiary analysis of genomic data. As next-generation sequencing (NGS) technology and the NGS market develops, the analysis, and interpretation of genomic data has proven to be one of the most complex aspects of transforming genomic data into meaningful results. Tertiary analysis, which follows primary and secondary analysis of the genomic data, is among the most challenging part. This is because tertiary analysis is key to how sequencing results are used. The core of tertiary analysis is "interpretation." Interpretation involves the biological classification of observed variants, determination of the clinical relevance of these variants, the deemed actionability of these variants in terms of treatment options, and extends to the ordering physician in terms of determining the usefulness of the results and recommendations. Tertiary analysis also includes multi-sample processing, quality attribution (QA) and quality control (QC) of variant calls, annotation and filtering of variants, data aggregation, association analysis, population structure analysis, and genome browser-driven exploratory analysis.

In one implementation, the genomic data comprises one or more variant call format (VCF) files (or genomic data files) 102. A VCF file, also called a genomic data file, is a text file that identifies gene sequence variations (variants) of an individual. VCF files 102 can be obtained from social genomics companies like 23andMe™ and Ancestry.com™. In one implementation, the VCF files 102 list single nucleotide polymorphisms (SNPs).

An application called "doc.ai" 106 is a platform that processes the genomic data of an individual and generates predictive analytics and personal health insights. Since the doc.ai application 106 is a consumer-facing application that runs on user devices like smartphones, tablets, and laptops, it is useful that it processes the genomic data efficiently and reports the results quickly. It is also desired to report the results using streamlined visualizations that are easily interpreted by the users. Low-latency analytics and intuitive user interface that enhance user experience and increase user retention may result.

Unimatrix

Unimatrix 108 supports the doc.ai application 106 on the back-end and ensures that the VCF files 102 uploaded 104 by the users on the doc.ai application 106 are processed efficiently. Unimatrix 108 accomplishes this by:

i. pushing 110 a VCF file onto a distributed cloud storage system like Google Cloud Storage (GCS)™ 112. GCS 112 indexes the entries in the VCF file and splits/partitions the VCF file into segments. GCS 112 then distributes the segments to multiple nodes 1-n of its distributed storage 122. GCS 112 also maintains a ledger of which range of indices of the VCF file entries are stored on which of the nodes 1-n.

ii. selecting a distributed, in-memory computing engine like Apache Spark 150 that has a dedicated connector (e.g., Spark Connector 134, See https://cloud.google.com/dataproc/docs/concepts/connectors/cloud-storage) for pulling the VCF file segments directly from the nodes 1-*n* of GCS 112 into its own distributed, in-memory computation nodes 170. In one implementation, the Spark Connector 134 indexes across the nodes 1-*n* of GCS 112 and loads respective VCF file segments onto corresponding in-memory computation nodes 1-*n* of Apache Spark 150. In some implementations, the indexes are stored on the nodes 1-*n* of GCS 112 along with the segments and are also transferred to the corresponding in-memory computation nodes 1-*n* of Apache Spark 150.

iii. executing distributed directives for tertiary analysis job contexts 160 directly on the VCF file segments stored on the in-memory computation nodes 1-*n* of Apache Spark 150, such that the VCF file segments are processed in parallel and the results are aggregated across the in-memory computation nodes 1-*n* to produce an output file 132. The output file 132 is visually rendered by a visualizer 158 according to pre-configured user interface design and is presented to the user via the doc.ai application 106. The visualized output file 132 is sent to the doc.ai application 106 via the GCS 112 and the Unimatrix 108.

Read-Only Storage of Genomic Data

Apache Spark 150 stores the VCF file segments (and/or their indexes) across the in-memory computation nodes 1-*n* that are read-only memories. We discovered that genomic data such as VCF files 102, and the results of tertiary analysis on the VCF files 102 do not have to be updated during their lifecycle and thus can be processed on read-only compute, without requiring file systems that manage read/write operations. Reading genomic data from the in-memory computation nodes 1-*n* is very efficient and reduces latency.

Querying Directly Against In-Memory Genomic Data

Efficiency is further enhanced by Spark SQL 152 that runs the tertiary analysis job contexts directly on the genomic data stored on the distributed, in-memory computation nodes 170. SQL statements that define the context of a tertiary analysis job are distributed by Spark SQL 152 across the in-memory computation nodes 1-*n* for execution using an SQL optimizer 154. SQL optimizer 154 takes an SQL statement, preprocesses it, and determines on which in-memory node it needs to be executed.

Figure 3:
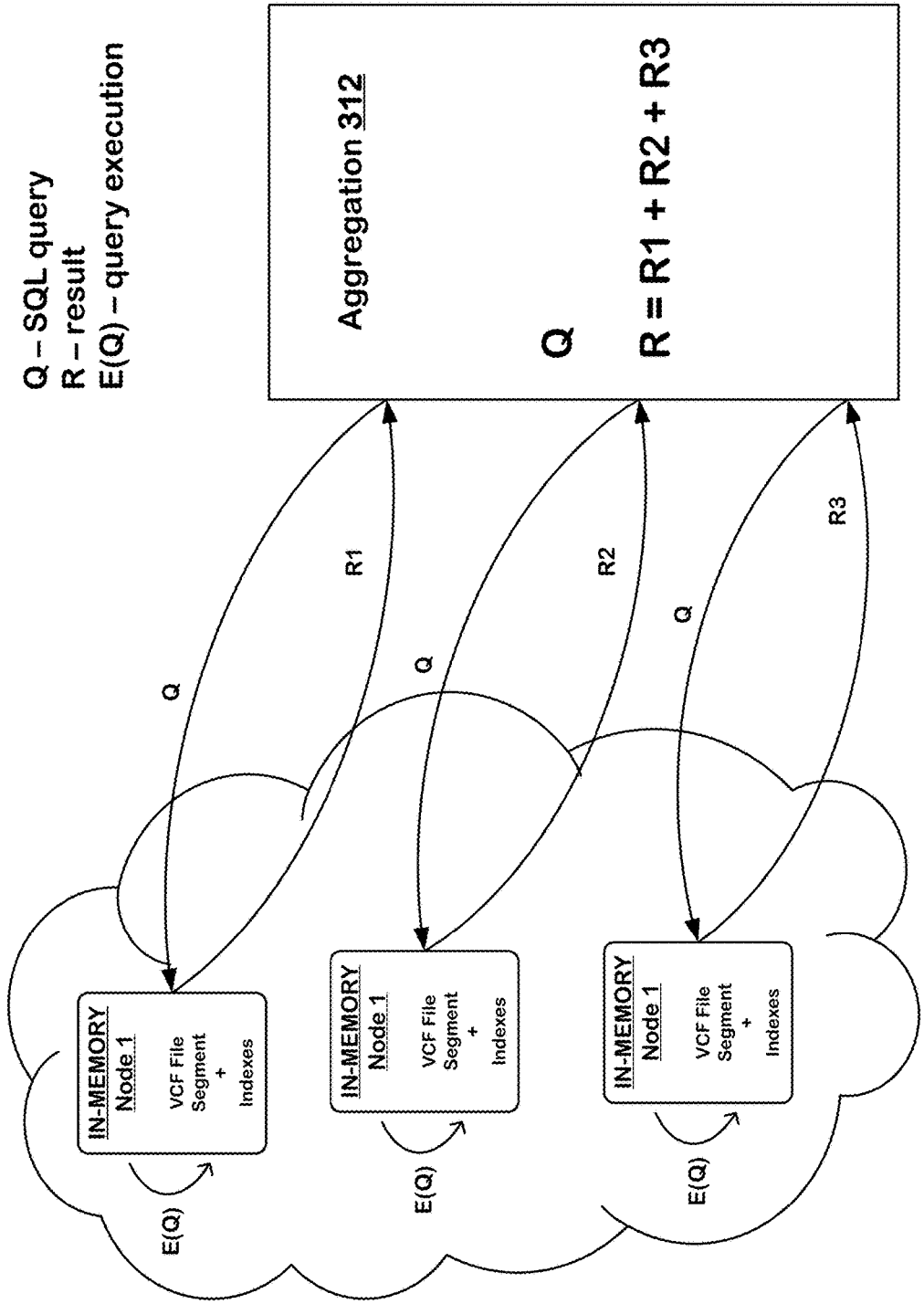
FIG. 3 discloses an accelerated processing pipeline for tertiary analysis of genomic data.

Spark SQL 152 supports distributed SQL functions such as joins and aggregations. As shown in the in-memory querying example 300 in FIG. 3, an SQL query is sent to all the nodes (Q) of a Spark Cluster 302 where data required for a join is located. The SQL query is then executed on every node (E(Q)) over the VCF file segments. Finally, the overall execution result (R) is aggregated 312.

This way, the SQL statements in the tertiary analysis job contexts 160 are agnostic to the addition or replacement of genomic data on the distributed, in-memory computation nodes 170 because Apache Spark 150 updates the indices of the genomic data in response to the addition or replacement, and redirects or redistributes the SQL statements to the corresponding in-memory computation nodes 1-*n* based on the updated indices.

Spark SQL 152 runs as a library on top of the distributed, in-memory computation nodes 170 of Apache Spark 150. Spark SQL 152 exposes SQL interfaces that can be accessed through a DataFrame API 156 integrated into programming languages supported by Apache Spark 150 (e.g., Python, Java, Scala, R). DataFrame API 156 allows developers to intermix procedural and relational code. A DataFrame is a distributed collection of rows with a homogeneous schema. A DataFrame is equivalent to a table in a relational database and can also be manipulated in similar ways. DataFrames support all common relational operators, including projection (select), filter (where), join, and aggregation. These operators build up an abstract syntax tree (AST) of the directive and pass it to the SQL optimizer 154.

FIG. 4 shows one implementation of converting a VCF file into a DataFrame.

Pre-Fetching Reference Dataset

Many tertiary analysis jobs require use of a reference dataset 180. Depending on the context of a tertiary analysis job, the reference dataset 180 can include human genomic reference sequence data for each chromosome along with gene locations, names, and coordinates; clinical interpretations of variants; annotated disease-causing variants, and so.

Efficiency is further enhanced by pre-fetching the reference dataset 180 to Apache Spark 150 and making it available in advance for the processing of the VCF file segments by the distributed, in-memory computation nodes 170. For example, if the tertiary analysis job requires identification of ancestry information by ethnic populations and/or sub-populations, then information, which identifies variants along with their ethnic attribution, is pre-populated at the reference data 180. When the VCF file segments are loaded onto the in-memory computation nodes 1-*n*, then a join is executed between the pre-fetched reference data 180 and the VCF file segments to determine the ethnic sources of the variants in the VCF file segments. Then, an estimation (e.g., percentage distribution) of the user's ethnic roots is encoded in the output file 132 and its visual representation is made available to the user via the doc.ai application 106.

In one implementation, the reference dataset 180 is pre-fetched to Apache Spark 150 in a so-called "Parquet" format (See https://docs.databricks.com/spark/latest/data-sources/read-parquet.html). Parquet is a columnar file format that provides optimizations to speed up queries and is a far more efficient file format than CSV or JSON (See https://docs.databricks.com/spark/latest/data-sources/read-parquet.html). Storing the reference dataset 180 in the Parquet format has many benefits such as faster execution of SQL queries, higher scan throughput, better performance with large-scale datasets, and others (See https://developer.ibm.com/hadoop/2016/01/14/5-reasons-to-choose-parquet-for-spark-sql/).

FIG. 5 shows one implementation of performing a join operation on a Parquet-style reference dataset 180.

Other Implementations

We have observed VCF files whose size ranges from one to a hundred megabytes (MB). The accelerated processing pipeline 100 is built: (1) to process VCF files greater than the observed sizes, (2) to process multiple VCF files in parallel, (3) to execute numerous SQL statements in parallel, and (4) to run multiple tertiary analysis jobs in parallel.

In one implementation, Apache Spark 150 runs on a cloud compute service like Amazon Web Services (AWS)™ 140 and is provided by a vendor like Databricks (See https://databricks.com/).

In one implementation, Unimatrix 108 is written in GO programming language (See https://golang.org/). In one implementation, Unimatrix 108 pushes the genomic data onto GCS 112 using a REST API. Once the genomic data is loaded onto the distributed storage 122 of GCS 112, Unimatrix 108 notifies Apache Spark 150 via a job trigger notification 180 that it can begin performing the tertiary analysis jobs (e.g., via another REST API).

Figure 2:
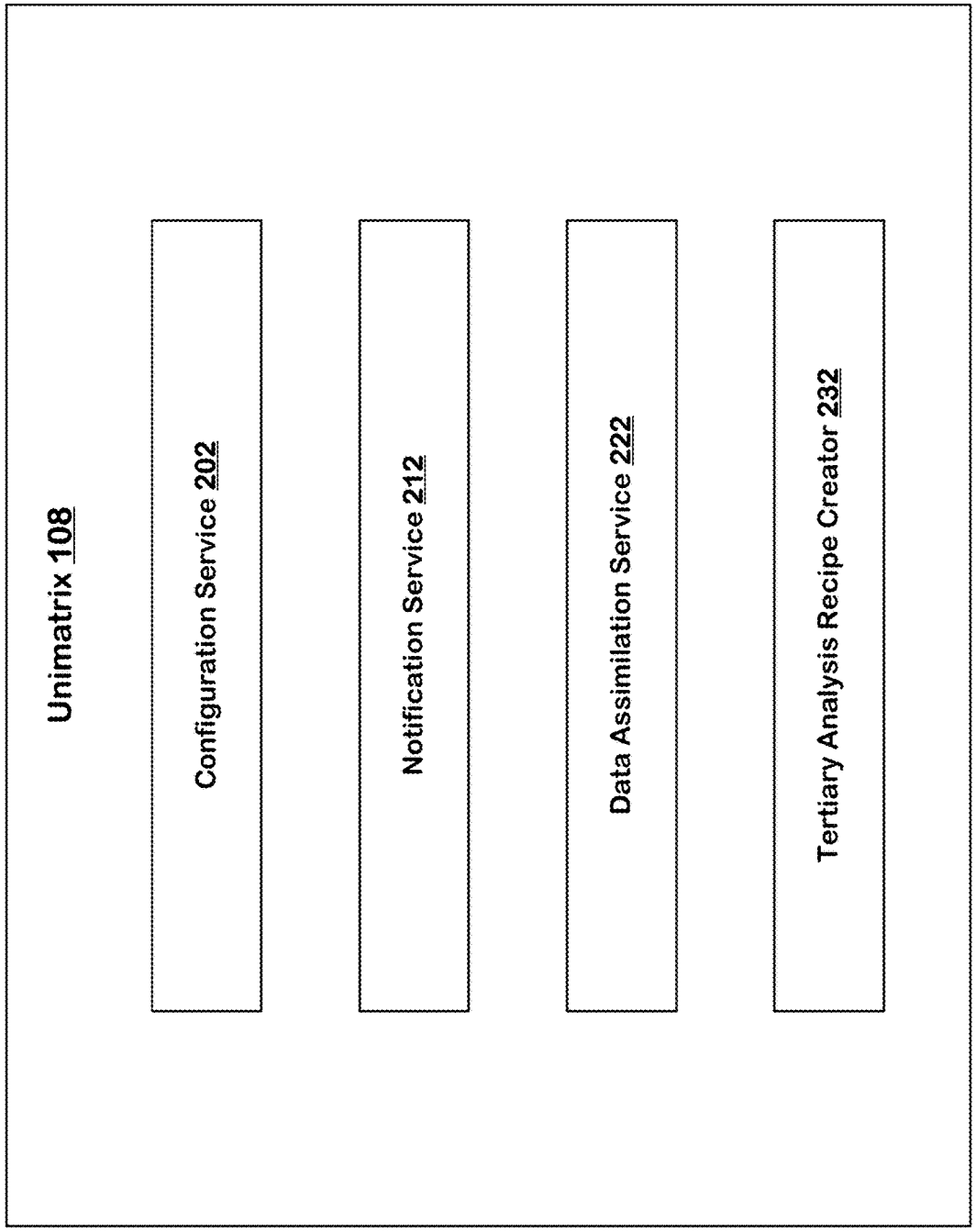
FIG. 2 shows example components of a Unimatrix engine.

FIG. 2 shows example components of Unimatrix 108. Unimatrix 108 comprises a configuration service 202 that sets up the tertiary analysis job contexts 160 at Apache Spark 150. Unimatrix 108 also comprises a notification service 202 that sends the job trigger notification 180 to Apache Spark 150.

Unimatrix 108 can also be considered an ingestion system that assimilates data from different sources. For example, a tertiary analysis job may require using a combination of clinical data from a lab (e.g., blood work report), medication prescription information from a drugstore, images of medication bottle labels, and genomic sequence data to produce a personalized health insight (e.g., calculation of a risk score of a user for an insurance company). In that case, Unimatrix 108 collects this combination of data from the different sources and makes them available for the accelerated processing 100 via a data assimilation service 222.

Unimatrix 108 also comprises a tertiary analysis recipe creator 232 that is an administrative interface for developers to program the context of tertiary analysis jobs (e.g., via SQL statements).

Unimatrix 108 can run ad-hoc/on-demand SQL queries in real-time and also periodically run SQL queries for updated genomic data and updated reference dataset 180.

The distributed, in-memory computation nodes 170 support atomicity, consistency, isolation, and durability (ACID) transactions and can be used with SQL, key-value, compute, machine learning, and other data processing APIs. The in-memory computation nodes 1-*n* are horizontally scalable.

In one implementation, the VCF file segments are kept in the distributed storage 122 of GCS 112 for backup and redundancy.

Technical Benefit

The technical benefit of the accelerated processing pipeline 100 is that it obviates the need for redundant application servers, applications, databases, and corresponding file systems, and thereby eliminates latency-causing data exchanges. For example, the accelerated processing pipeline 100 does not use an application server to upload the genomic data to a file system via file transfer protocol (FTP). It also does not need a first application to load the genomic data to a database. It also does not need a second application to process the genomic data and to write the results back to the database. The results do not have to be sent back to the application server for display to the user. Therefore, computational resources are saved and computation and delivery time are reduced.

Streamlined Germline Browser

The discussion now turns to the "streamlined germline browser" of the doc.ai application 106. As a provisioning step, a user using the streamlined germline browser uploads his genomic data to the doc.ai application 106. The genomic data can be VCF files 102.

Edge Computing

In a so-called "edge" implementation, the genomic data does not leave the user's device (e.g., smartphones, tablets, and laptops) on which the doc.ai application 106 is running and onto which the user uploads his genomic data. In such an implementation, the user's genomic data is processed on the user's device and not uploaded to a server or a cloud storage system. On-device databases such as PostgreSQL can be used to store and process the user's genomic data locally on the user's device.

1. Search Interface

Figure 6:
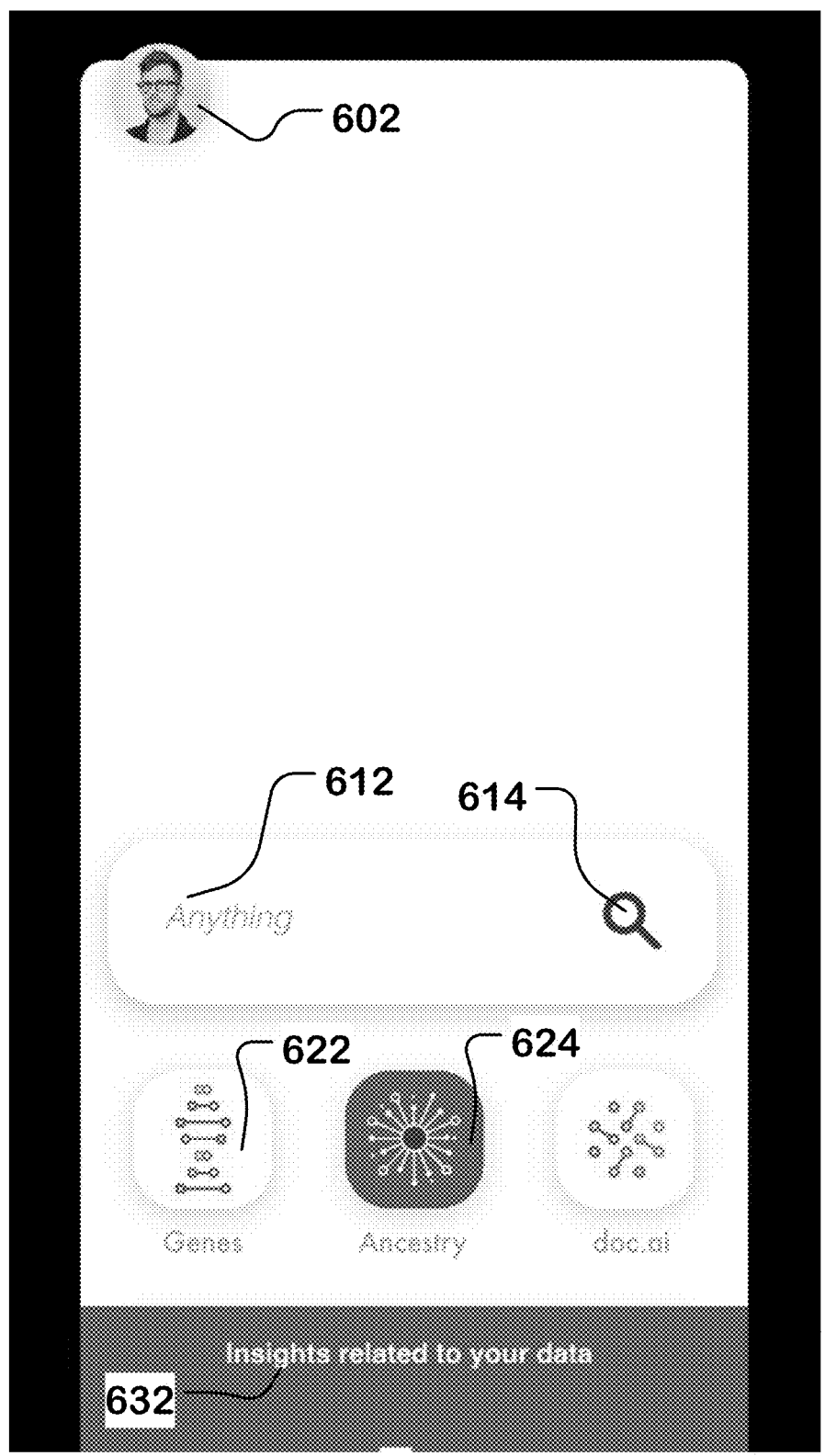
FIG. 6 shows an example search interface of a streamlined germline browser.

FIG. 6 shows a search interface 600 of the streamlined germline browser. The search interface 600 shows an image 602 of the user.

The search interface 600 has a text entry box 612 in which the user can enter the name of a particular trait (e.g., blue eyes, fire toes) and search 614 his genomic data to see which variants/mutations (e.g., single nucleotide polymorphisms (SNPs), indels) in his genetic sequences caused expression of the particular trait and where such variants are located.

Similarly, the user can search 614 his genomic data for whether he is susceptible to a particular trait (e.g., skin keratosis). If the user is susceptible to the particular trait, then the user can see which variants (e.g., SNPs, indels) in his genetic sequences would cause expression of the particular trait and where such variants are located.

The user can also enter the name of a particular disease (e.g., asthma, diabetes 2, fast twitch muscles, B12 absorption) and search 614 his genomic data to see which variants (e.g., SNPs, indels) in his genetic sequences caused the particular disease and where such variants are located.

Similarly, the user can search 614 his genomic data for whether he is susceptible to a particular disease (e.g., cancer). If the user is susceptible to the particular disease, then the user can see which variants (e.g., SNPs, indels) in his genetic sequences would cause the particular disease and where such variants are located.

2. Insights Interface

Figure 7:
FIG. 7 depicts an example insights interface of the streamlined germline browser.
Figure 8:
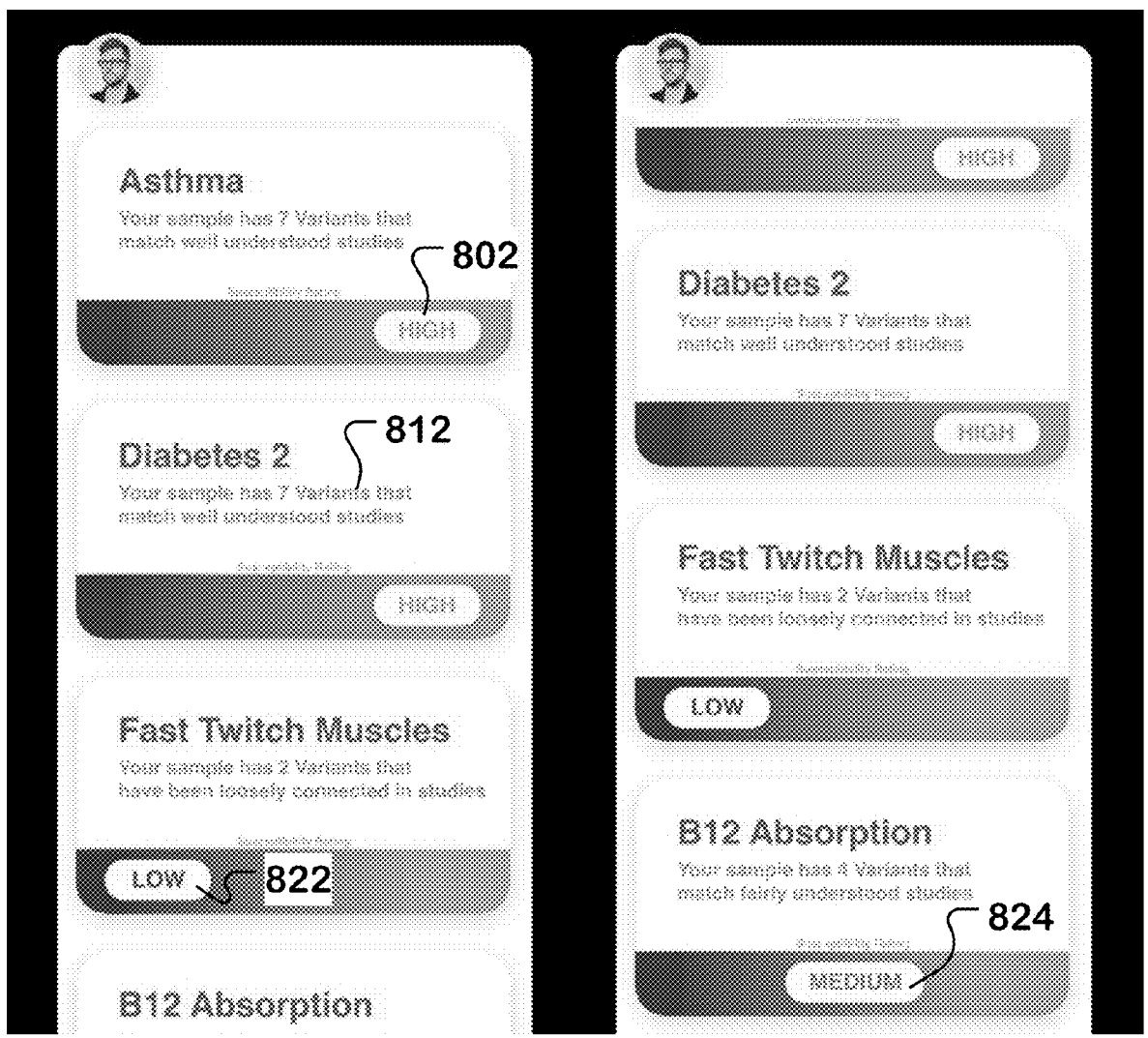
FIG. 8 illustrates an example susceptibility rating interface of the streamlined germline browser.

Insights interface 700 presents certain insights 632 to the user, an example of which is depicted in FIG. 7. Insights interface 700 also has an "I Understand" button 702. When the user selects the "I Understand" button 702, a susceptibility rating interface 800 is presented to the user.

3. Susceptibility Rating Interface

Susceptibility rating interface 800 lists which diseases the user is susceptible to based on the presence of certain variants in his genetic sequences. With every listed disease, the susceptibility rating interface 800 also provides a brief narrative 812 that tells the user a count of the variants that cause the particular disease and that the disease-causing character of the variants is known based on clinical studies and/or publications.

Susceptibility rating interface 800 provides the following susceptibility ratings: high 802, medium 824, and low 822. A high susceptibility rating 802 is given when the user's genetic sequences have a threshold number of those variants that are reliably known to cause the particular disease based on several clinical studies and/or publications.

A medium susceptibility rating 824 is given when the user's genetic sequences do not have a sufficient number of those variants that can be reliably associated with the particular disease, or when only a sparse number of clinical studies and/or publications support the disease-causing character of the variants (i.e., when there is not enough research on this topic to give the user a High or Low susceptibility of this being an issue), or when there are conflicting clinical studies and/or publications. A medium susceptibility rating 824 can also occur when the genetic sequences uploaded by the user contain only a portion of the user's genomic data, instead of the entire genome.

A low susceptibility rating 822 is given when the user's genetic sequences have less than a ceiling number of those variants that can be reliably associated with the particular disease (i.e., when few to none of the user's genes are connected to the particular disease), or when there is scant or conflicting evidence supporting the disease-causing character of the variants.

4. Per-Disease, Cross-Chromosomes Interface

When the user clicks on a particular disease on the susceptibility rating interface 800, the streamlined germline browser generates a per-disease, cross-chromosomes interface 900 for that particular disease.

Figure 9:
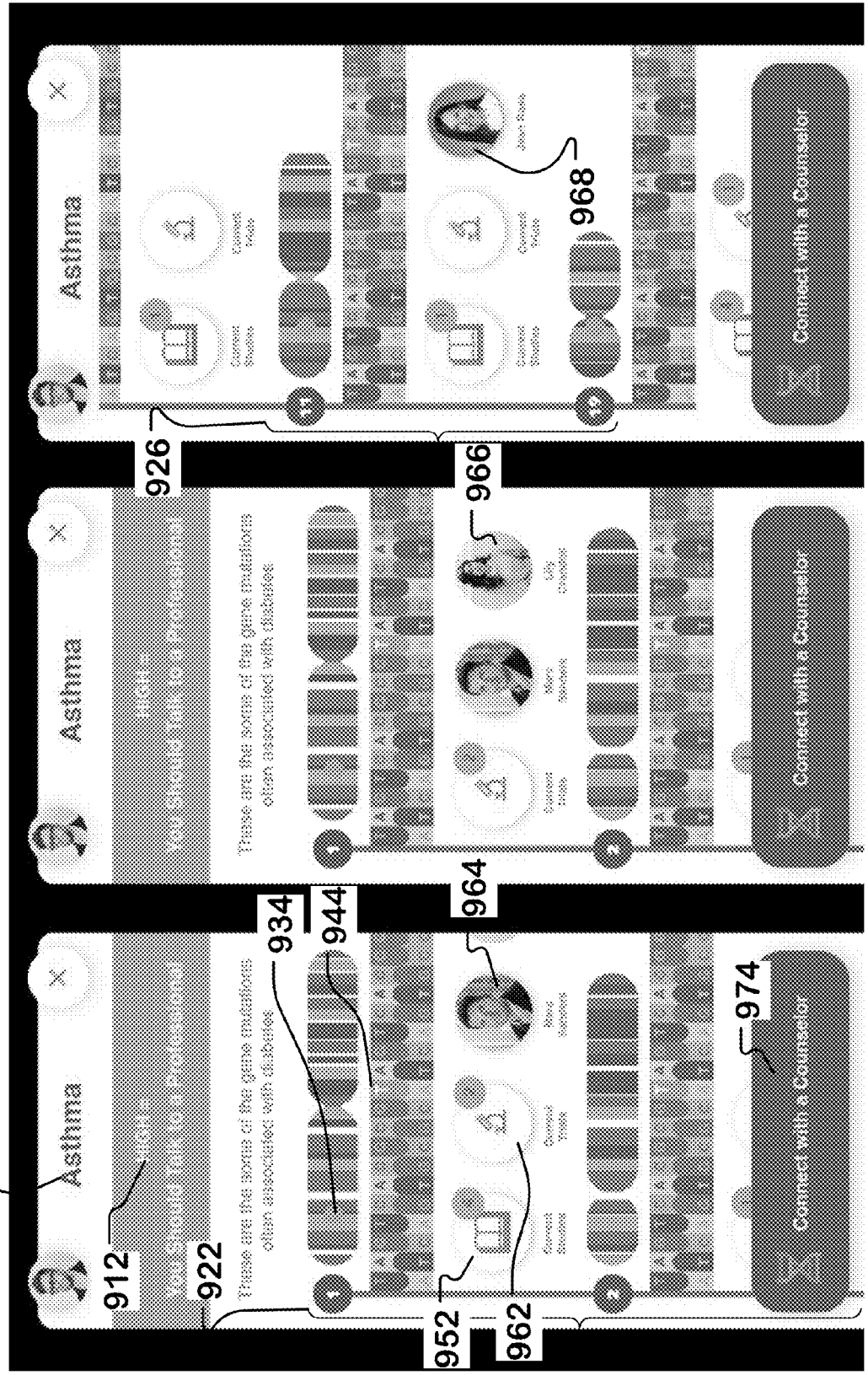
FIG. 9 shows an example per-disease, cross-chromosomes interface of the streamlined germline browser.

One example of the per-disease, cross-chromosomes interface 900 for asthma 902 is shown in FIG. 9 and has the following features:

i. A visual depiction 922, 926 of each of the twenty-two chromosomes and the two sex chromosomes, such that the user can scroll/navigate up and down to view the different chromosomes, along with variants on some or all of the different chromosomes that cause a particular disease such as asthma 902. The chromosomes can be arranged in a descending or ascending order, or prioritized based on the level of their contribution/association to asthma 902. Thus, the per-disease, cross-chromosomes interface 900 spans across and covers all the chromosomes.

ii. Each chromosome's visual depiction has a backed-up view 934 that highlights one or more asthma-causing variants that are present in the chromosome.

iii. Each chromosome's visual depiction has a zoomed-in view 944 that highlights the nucleotide bases of its asthma-causing variants (e.g., nucleotide base "T" on chromosome 1, nucleotide base "G" on chromosome 19).

iv. Each chromosome's visual depiction is supplemented by access to one or more current clinical studies and/or publications 952 that focus on and describe the asthma-causing character of the variants.

v. Each chromosome's visual depiction is supplemented by access to one or more current trials 962 that are exploring the asthma-causing character of the variants.

vi. Each chromosome's visual depiction is supplemented by access to one or more genetic counselors 964, 966, 968 that specialize in (1) the corresponding chromosome, (2) the corresponding variant, and/or (3) the corresponding disease, i.e., asthma 902. Note that different chromosomes and their variants can have different genetic counselors that respectively specialize in them (e.g., genetic counselor 964 ("Marc Sanders") for chromosome 1 v/s genetic counselor 968 ("Jean Ross") for chromosome 11).

vii. Each chromosome's visual depiction is supplemented by a link 974 to connect to a particular genetic counselor. When the user clicks on link 974, then the streamlined germline browser directs the user to the particular genetic counselor's webpage or to other contact information.

viii. Per-disease, cross-chromosomes interface 900 also recommends 912 to the user what actions he should take based on the susceptibility rating assigned to the disease (e.g., "you should talk to a profession").

5. Studies and Publications Interface

Figure 10:
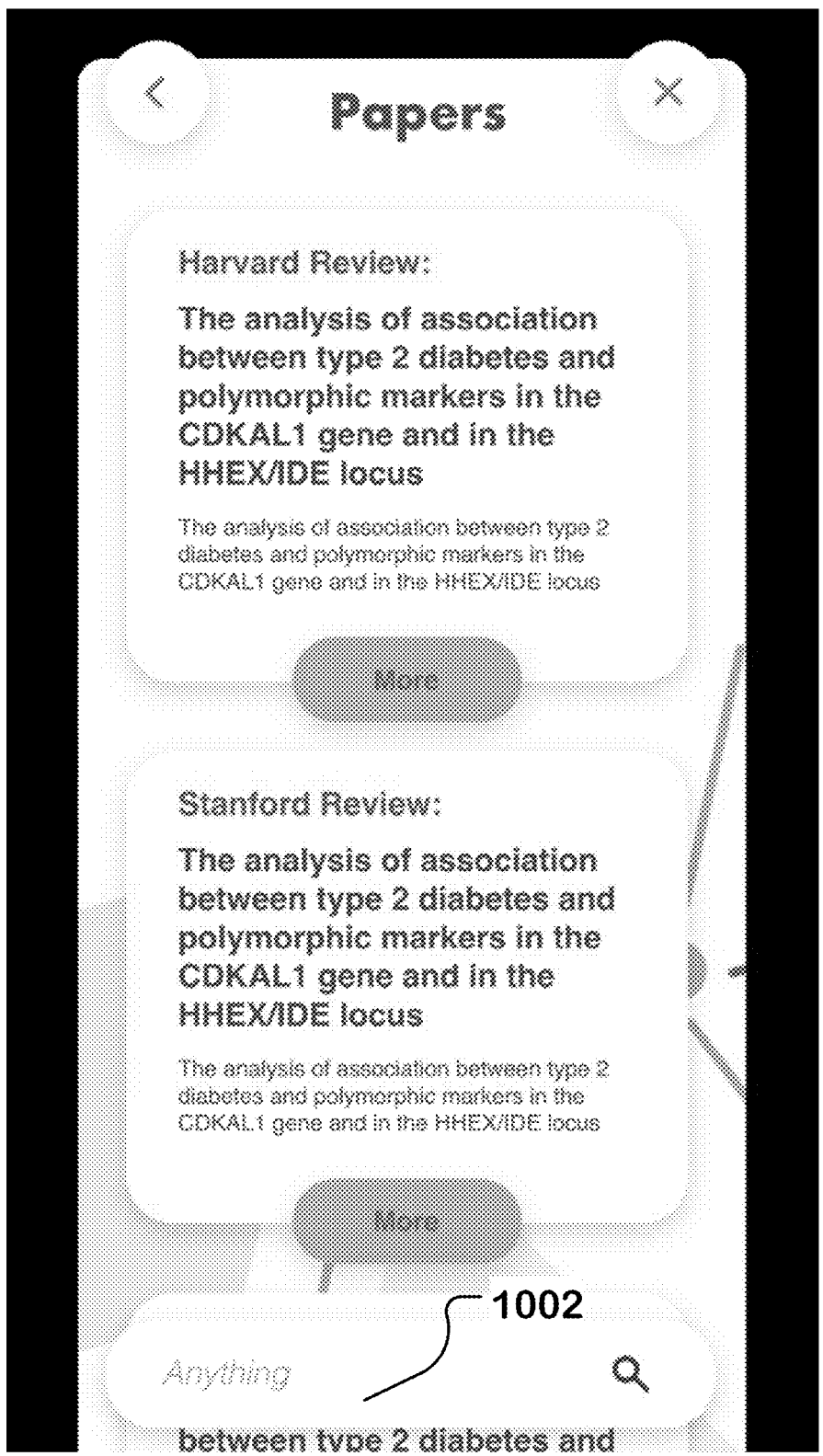
FIG. 10 depicts an example studies and publications interface of the streamlined germline browser.

When the user clicks on the user interface widget representing/providing access to the current clinical studies and/or publications 952, then a studies and publications interface 1000 is presented to the user (FIG. 10). Studies and publications interface 1000 lists the current clinical studies and/or publications 952 and also provides a search box 1002 for the user to search for specific studies and/or publications or their content (e.g., authorship) based on keywords.

6. Trials Interface

Figure 11:
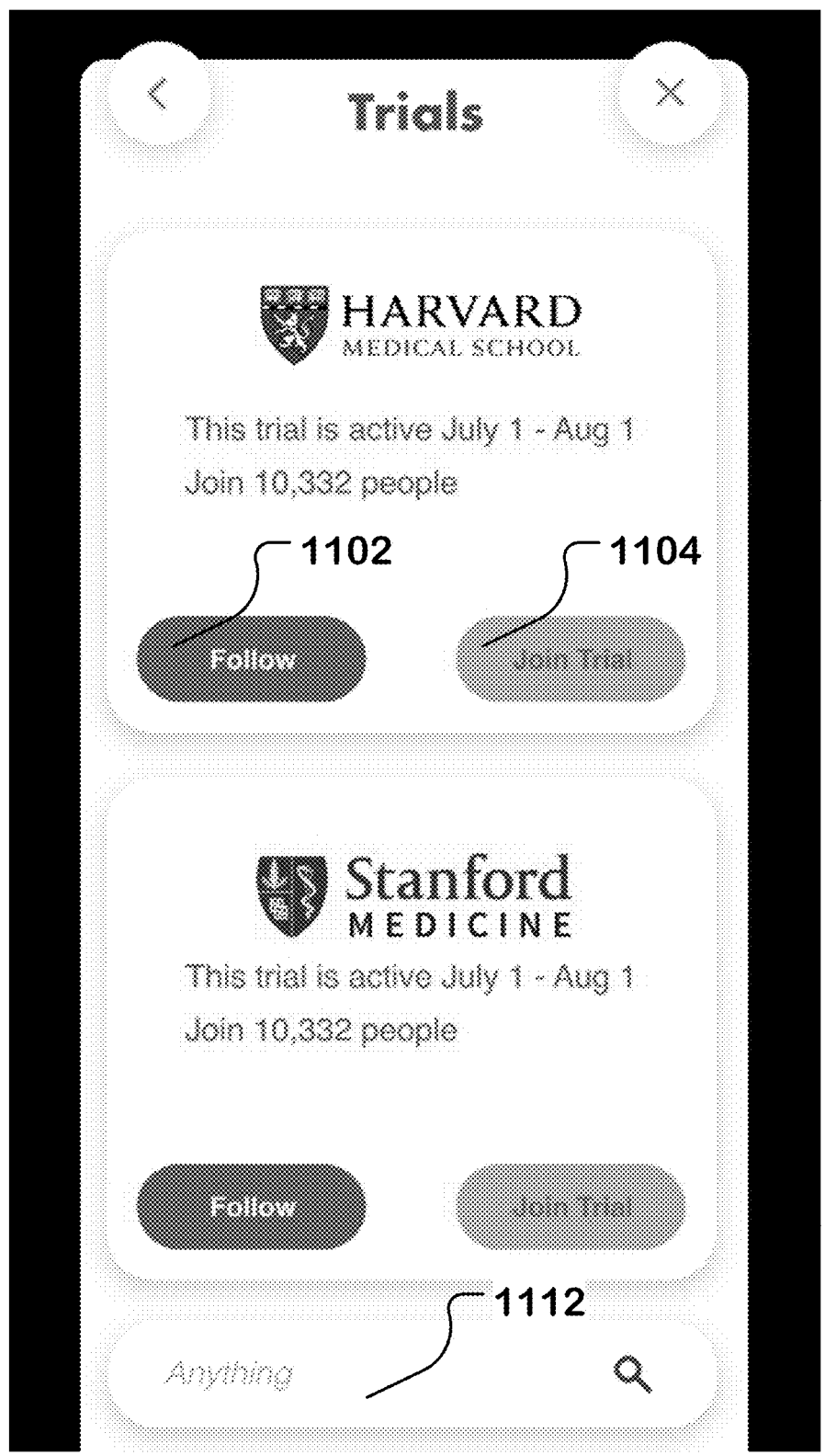
FIG. 11 illustrates an example trials interface of the streamlined germline browser.

When the user clicks on the user interface widget representing/providing access to the current trials 962, then a trials interface 1100 is presented to the user (FIG. 11). Trials interface 1100 lists the current trials 962 and also provides a search box 1112 for the user to search for specific trials or their content (e.g., institution) based on keywords.

Trials interface 1100 also allows the user to follow 1102 a particular trial and/or join 1104 the particular trial. This is especially useful because clinical trials have to spend a great deal of time and effort recruiting individuals that suffer from the disease that is the subject of a clinical trial. With the technology disclosed, the users can report themselves to the clinical trials that are studying the disease they have (i.e., with just few clicks on the streamlined germline browser).

7. Multiple Diseases, Per-Chromosome Interface

When the user clicks on a genes widget 622 of the search interface 600, the streamlined germline browser generates a multiple diseases, per-chromosome interface 1200 for the user.

Figure 12:
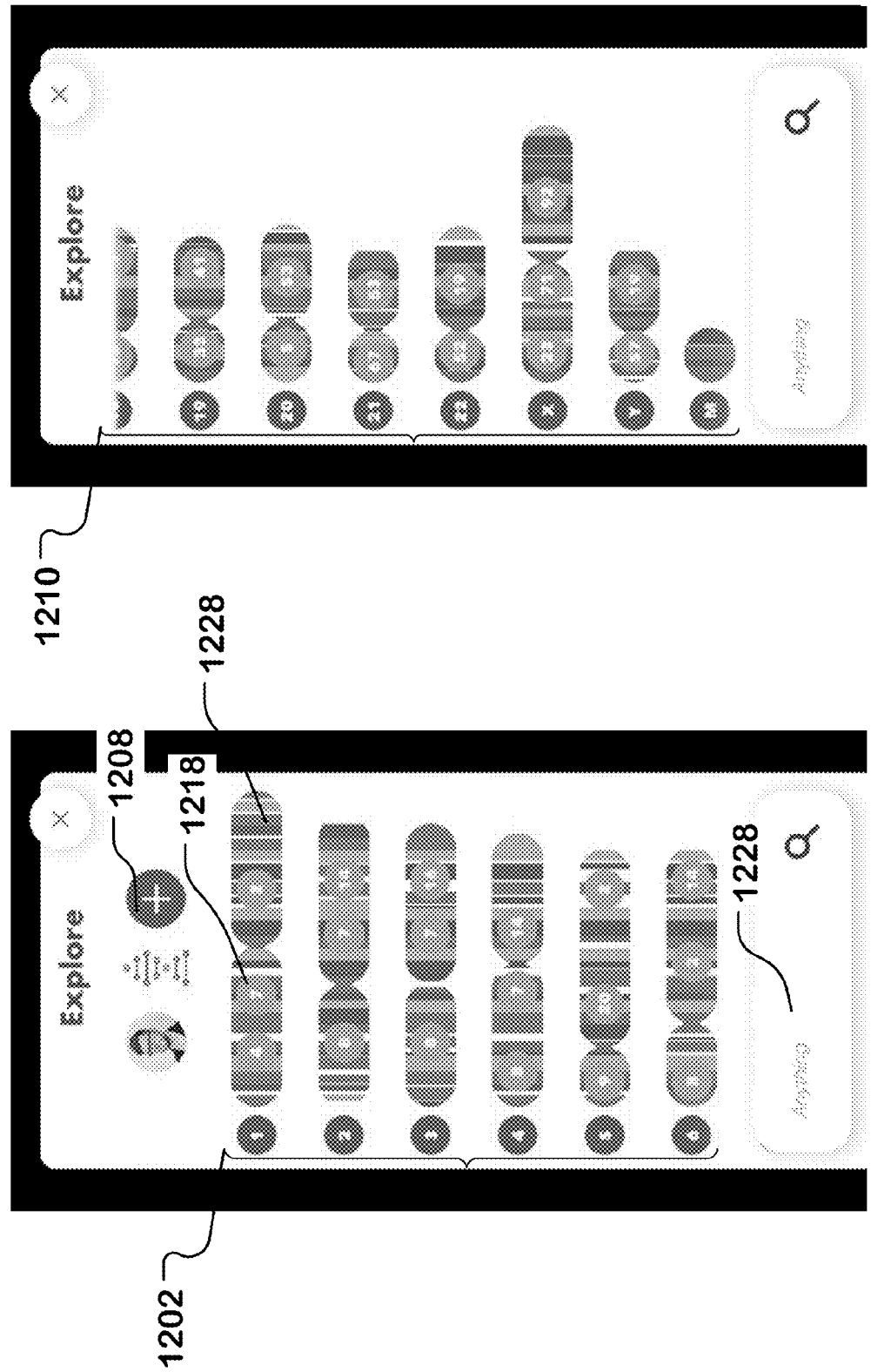
FIG. 12 shows an example multiple diseases, per-chromosome interface of the streamlined germline browser.
Figure 13:
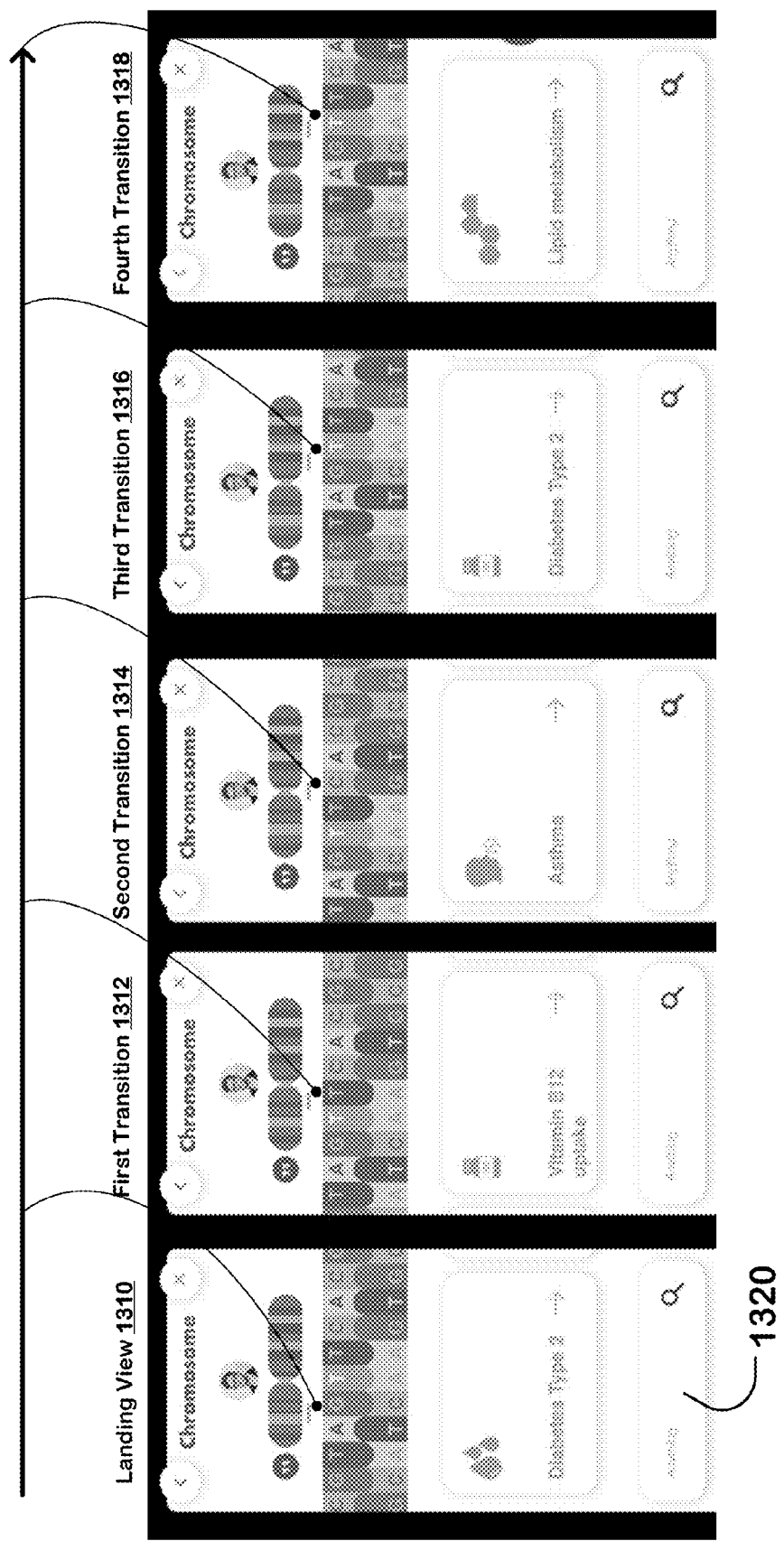
FIG. 13 depicts an example per-chromosome zoomed-in view of the streamlined germline browser.

One example of the multiple diseases, per-chromosome interface 1200 is shown in FIG. 12 and has the following features:

ix. A visual depiction 1202, 1210 of each of the twenty-two chromosomes and the two sex chromosomes, such that the user can scroll/navigate up and down to view the different chromosomes, along with a visual depiction of one or more diseases (e.g., diabetes type 2, vitamin B12 uptake, asthma, lipid metabolism) caused by variants on each of the different chromosomes. The chromosomes can be arranged in a descending or ascending order, or prioritized based on the number of diseases with which they are associated. Thus, the multiple diseases, per-chromosome interface 1200 spans across and covers all the chromosomes, and also covers/depicts a plurality of diseases per chromosome.

x. Each chromosome's visual depiction has a backed-up view 1228 that highlights counts 1218 of the disease-causing variants, which are grouped by diseases and are spread across a chromosome's visual depiction.

xi. A search box 1228 that allows the user to filter the multiple diseases, per-chromosome interface 1200 by diseases.

xii. When the user clicks on a particular chromosome (e.g., chromosome 11), a zoomed-in view 1300 of the particular chromosome is presented to the user. Zoomed-in view 1300 (FIG. 13) shows the different diseases (e.g., diabetes type 2, vitamin B12 uptake, asthma, lipid metabolism) that are caused by the different variants occurring on the particular chromosome. The user can traverse 1302 through the visual depiction of the particular chromosome and move from one disease to the next (e.g., landing view 1310 to first transition 1312 to second transition 1314 to third transition 1316 to fourth transition 1318). Within the zoomed-in view 1300 of the particular chromosome, the diseases are arranged by whose variants occur at the beginning of the particular chromosome (e.g., diabetes type 2) and progressively transition to diseases with later occurring variants (e.g., vitamin B12 uptake, asthma, lipid metabolism). Some diseases that have variants before and after the variants of another disease are repeated (e.g., diabetes type 2 in third transition 1316). In some implementations, each depicted disease in the zoomed-in view 1300 is supplemented with a depiction of the nucleotide bases of the variants associated with the disease. A search box 1320 allows the user to filter the zoomed-in view 1300 by diseases.

8. Connect Interface

When the user clicks on a connect widget 1208 of the multiple diseases, per-chromosome interface 1200, the streamlined germline browser generates a connect interface 1400 for the user.

Figure 14:
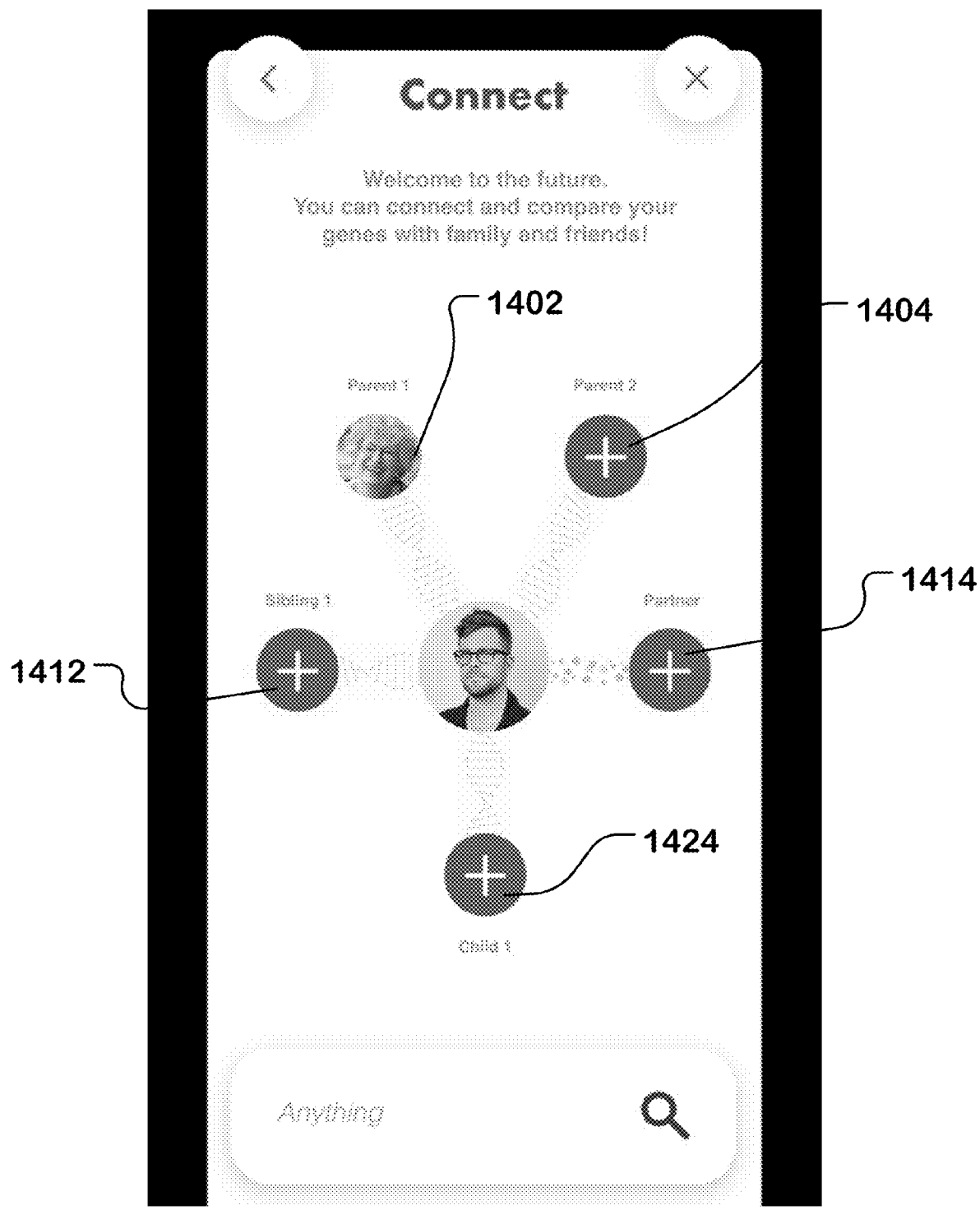
FIG. 14 illustrates an example connect interface of the streamlined germline browser.

Connect interface 1400 of FIG. 14 allows the user to compare his genetic information with that of another individual such as a first parent 1402, a second parent 1404, a first sibling 1412, a second sibling, a first child 1424, a second child, and a partner 1404.

Figure 15:
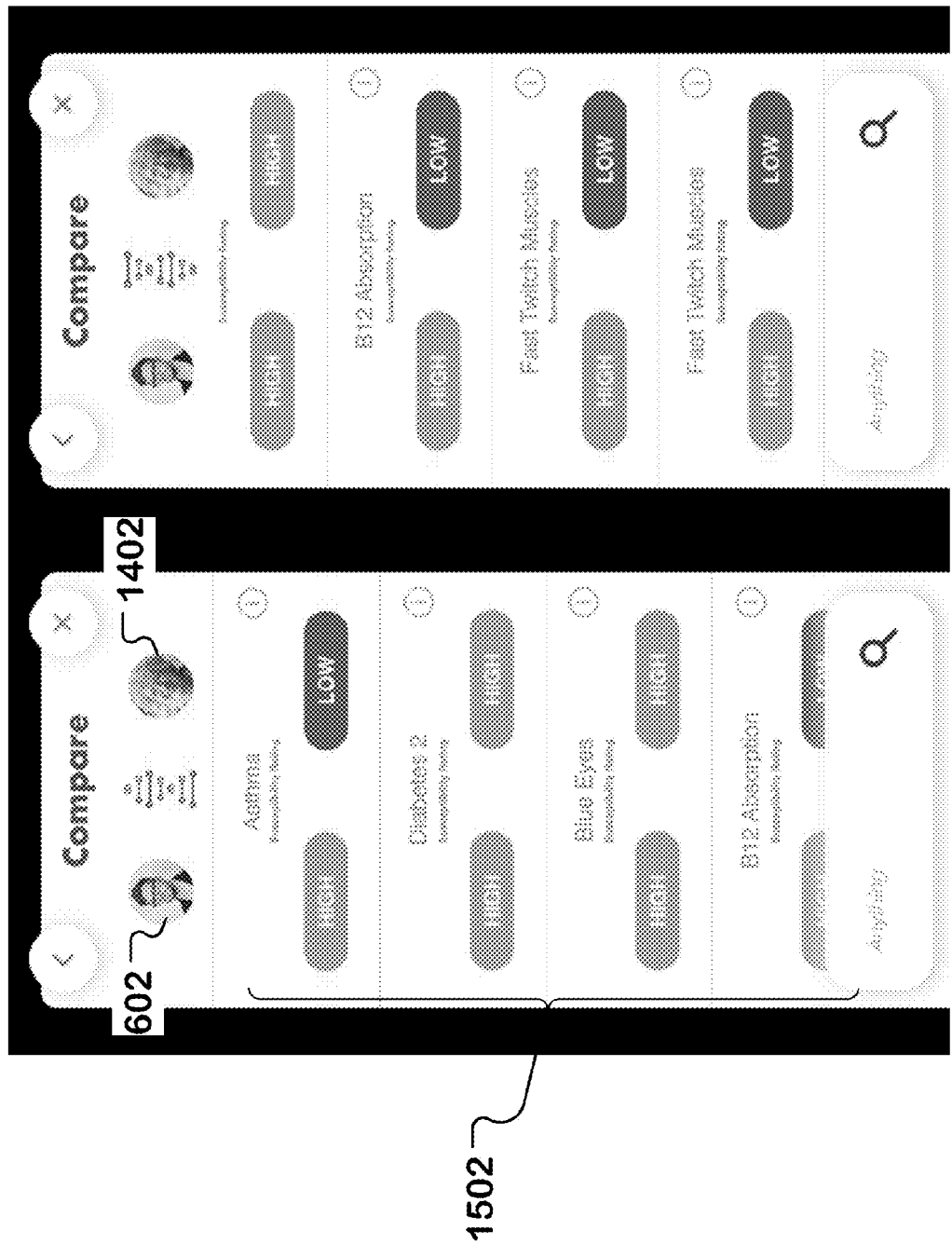
FIG. 15 shows an example comparison interface of the streamlined germline browser.

The following implementations assume that genomic data of the other individual with whom the user wants to compare his health insights is already available on the user's device on which the doc.ai application 106 runs. In such implementations, the connect interface 1400 uses the genomic data of the user and the genomic data of the other individual and separately processes them to generate their respective susceptibility ratings for different diseases. The results of such analysis are visually displayed by a comparison interface 1500 of FIG. 15. In one implementation, the comparison interface 1500 shows the susceptibility ratings of the user 602 and his mother 1402 for corresponding diseases next to each other 1502.

In one implementation, the genomic data of the user and the genomic data of the other individual are stored and processed on the user's device on which the doc.ai application 106 runs. This is referred to as the "edge computing" implementation in which the genomic data does not leave the user's device on which the doc.ai application 106 runs and is not sent to a server or to a cloud storage system for storage or processing. Similarly, the results of the processing (e.g., susceptibility ratings for different diseases of the user and the other individual) are kept only on the user's device on which the doc.ai application 106 runs.

Such a visual depiction can help the user infer whether he inherited a particular disease-susceptibility from his mother or his father. That is, if the user has a high susceptibility for asthma, but his mother has a low susceptibility for asthma, then it is likely that the user inherited asthma-susceptibility from his father. In contrast, if the user and his mother both have high susceptibility for diabetes 2, then it is likely that the user inherited diabetes-susceptibility from his mother.

Partner Compatibility

In other implementations, such a comparative analysis may be used by prospective partners to determine whether they are a good fit for each other (e.g., as a compatibility factor on a dating site or application). This can be the case because if both the prospective partners have high susceptibility for certain diseases (e.g., fatal diseases like cancer), then it is likely that their children/offsprings would be susceptible to such diseases. Such a comparative analysis can overtime minimize instances of commonly-susceptible people having children and ultimately lead to the eradication of life-threatening diseases like cancer or elimination of disease-causing allele like human leukocyte antigen (HLA).

Figure 16:
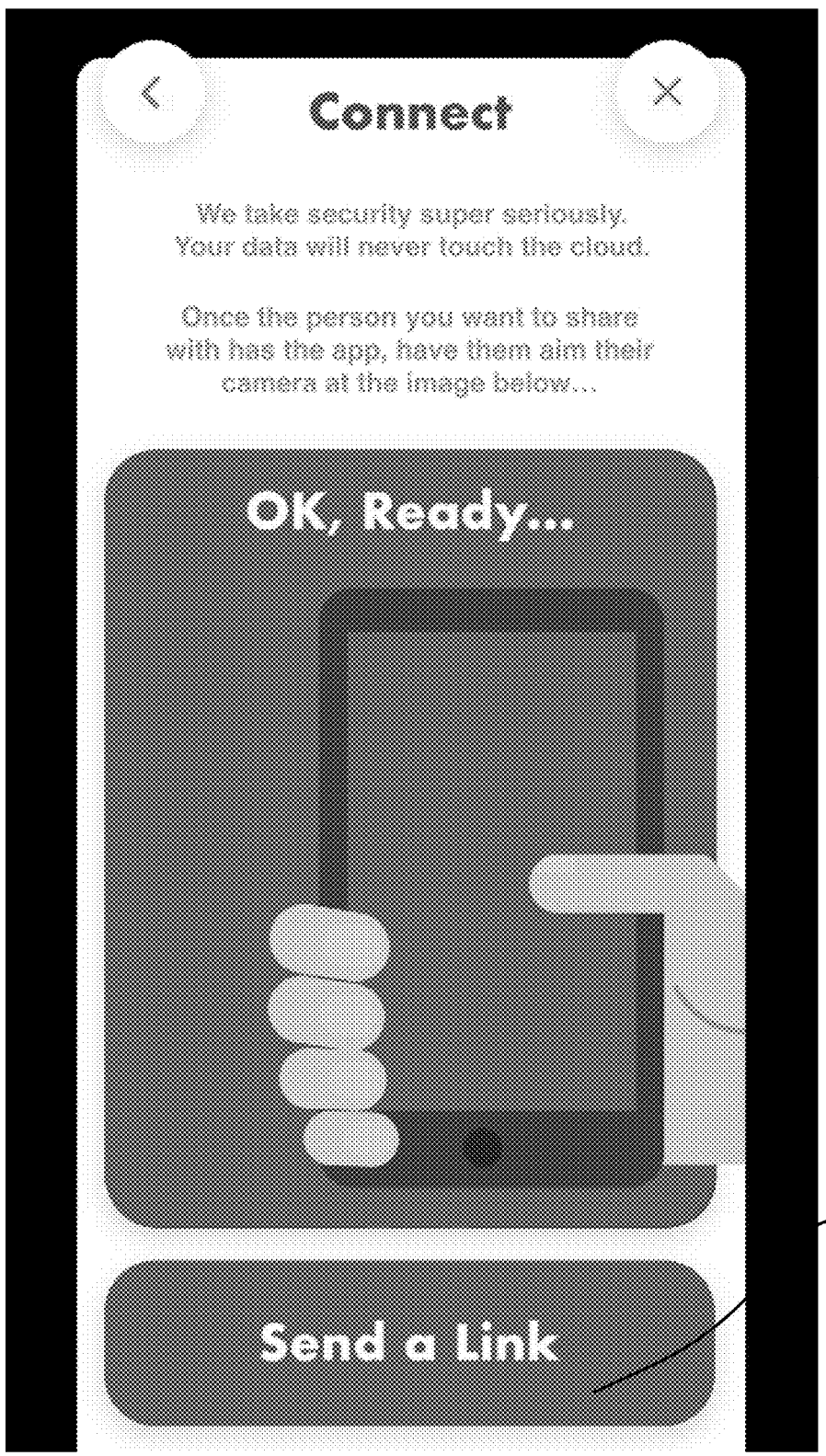
FIG. 16 depicts an example invite interface of the streamlined germline browser.

When the user wants to compare his health insights with an individual whose genomic data is not already loaded onto the user's device on which the doc.ai application 106 runs, then the user has to invite the other individual to share his or her genomic data with the user. This is accomplished by an invite interface 1600 (FIG. 16) that has a "Send a Link" button 1602. When the user selects the "Send a Link" button 1602, an image sequence interface 1700 is presented to the user.

Figure 17:
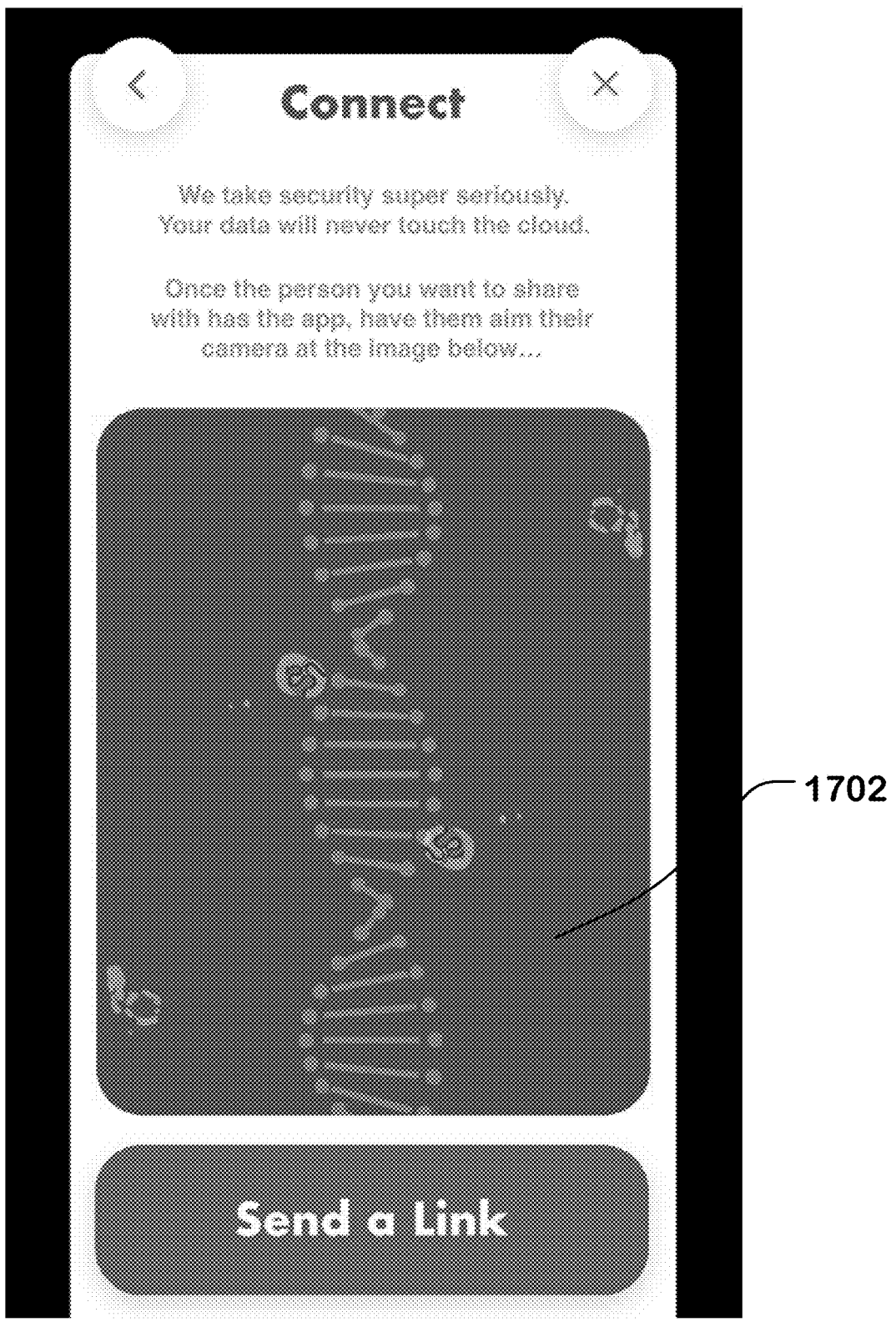
FIG. 17 illustrates an example image sequence interface of the streamlined germline browser.
Figure 18:
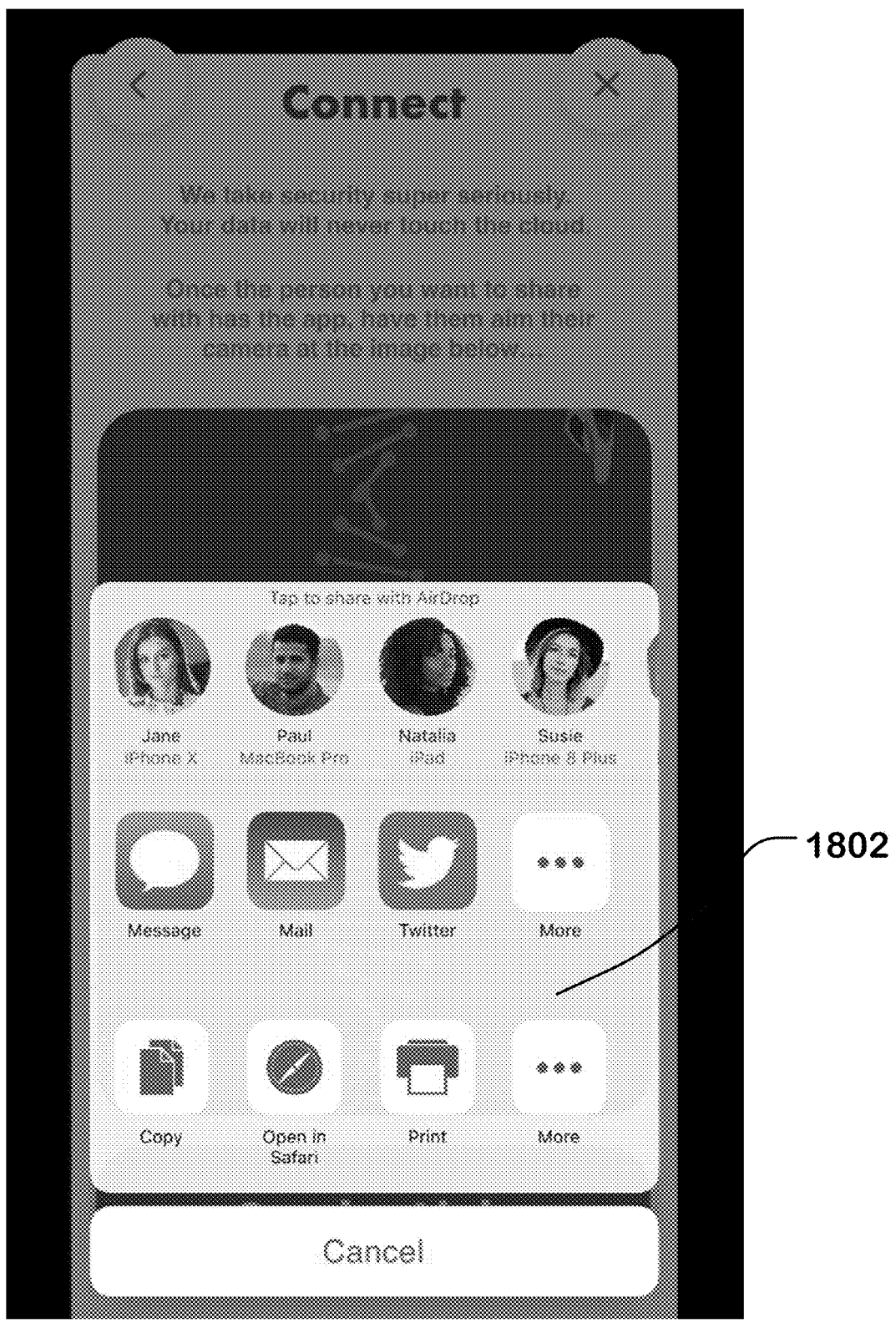
FIG. 18 shows an example share interface of the streamlined germline browser.
Figure 19:
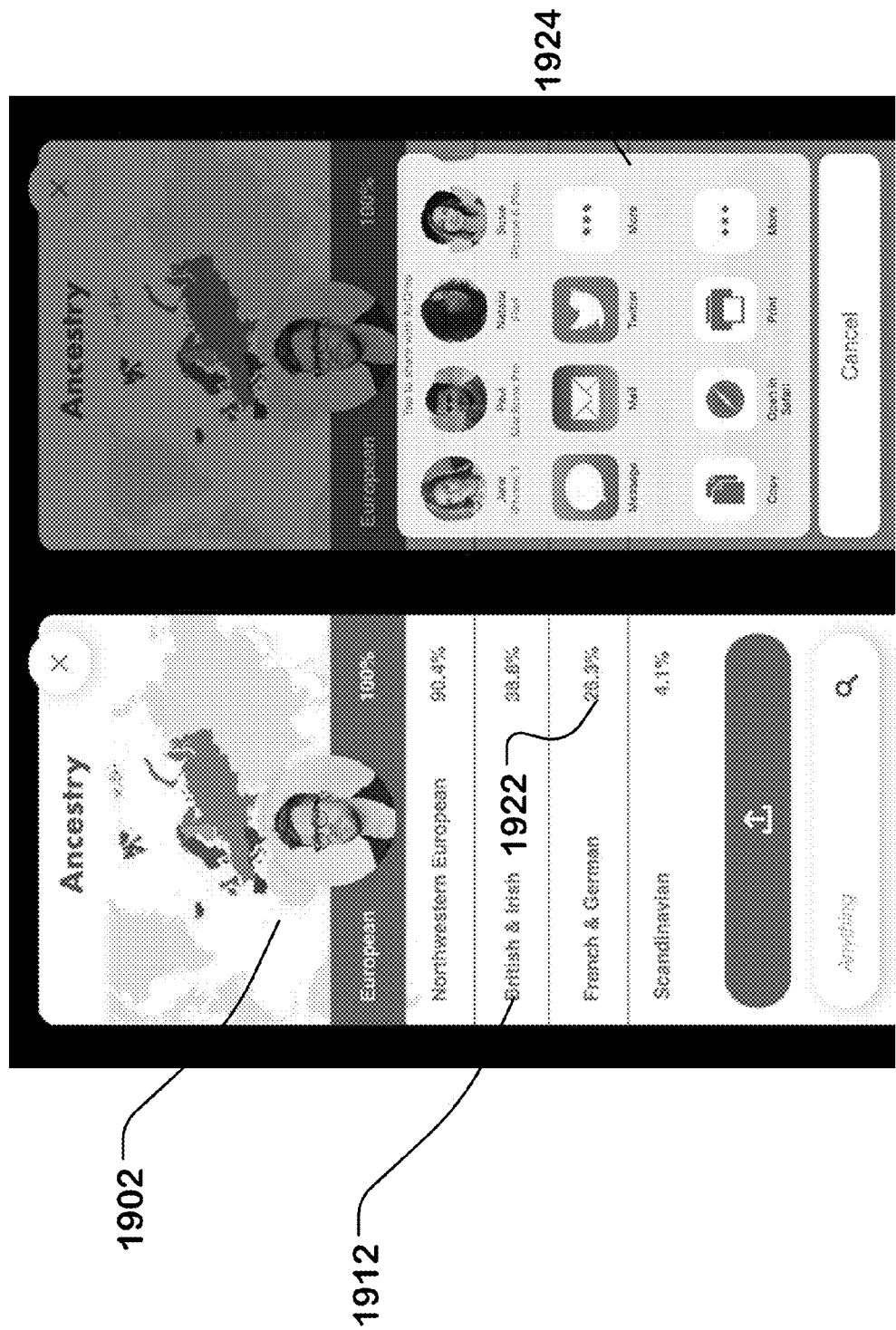
FIG. 19 depicts an example ancestry interface of the streamlined germline browser.

Image sequence interface 1700 (FIG. 17) contains an encrypted image 1702 (e.g., of a spinning double-stranded helix DNA) that the user can share with the other individual over text or other commonly-used communication channel 1802 (e.g., social media post). The sharing can be performed via a share interface 1800.

The other user can then scan the encrypted image 1702 from his or her phone's camera (e.g., like a quick response (QR) code scan) for authentication and start sharing his or her genomic data with the user (e.g., over a Bluetooth channel). In some implementations, the other individual's consent and approval for specific and/or time-bound use of his or her genomic data may be received and recorded.

Once the user's device receives the other individual's genomic data, then comparative analysis like the one discussed with respect to the comparison interface 1500 can be performed.

In some implementations, once the other individual's genomic data is used for the comparative analysis, it can be automatically erased from the user's device. This ensures that the other individual's genomic data is not used beyond the purposes to which he or she consented. Similarly, a decay factor may be used to erase the other individual's genomic data after a certain period of time.

9. Ancestry Interface

When the user clicks on an ancestry widget 624 of the search interface 600, the streamlined germline browser generates an ancestry interface 1900 for the user. Ancestry interface 1900 shows the user's ethnic origins 1912 along with corresponding makeup percentages 1922 and a color-coded or heated map 1902 of the countries or geographic regions to which the ethnic origins 1912 belong. The user can also share this visual information with others via commonly-used communication channels 1924 (e.g., text, social media post).

10. Disease Auto-Suggest Interface

Figure 20:
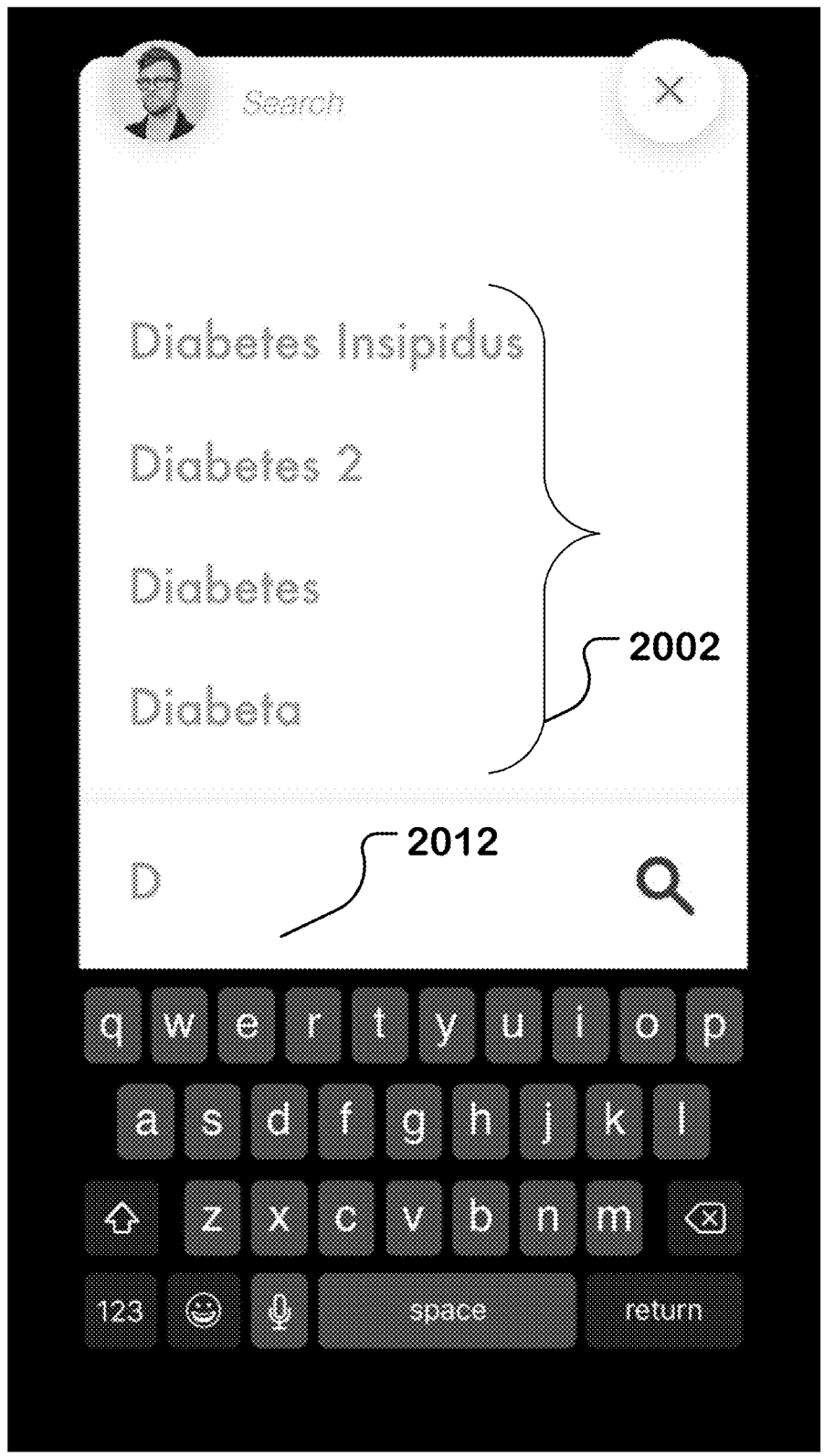
FIG. 20 illustrates an example disease auto-suggest interface of the streamlined germline browser.

FIG. 20 shows one implementation of a disease auto-suggest interface 2000. When the user enters some text into a search box 2012 of the streamlined germline browser to specify a disease (or trait), the user can be presented with automatically suggested disease (or trait) names 2002 that are responsive to the text entered by the user.

Poly-Omics Pipeline

Figure 21:
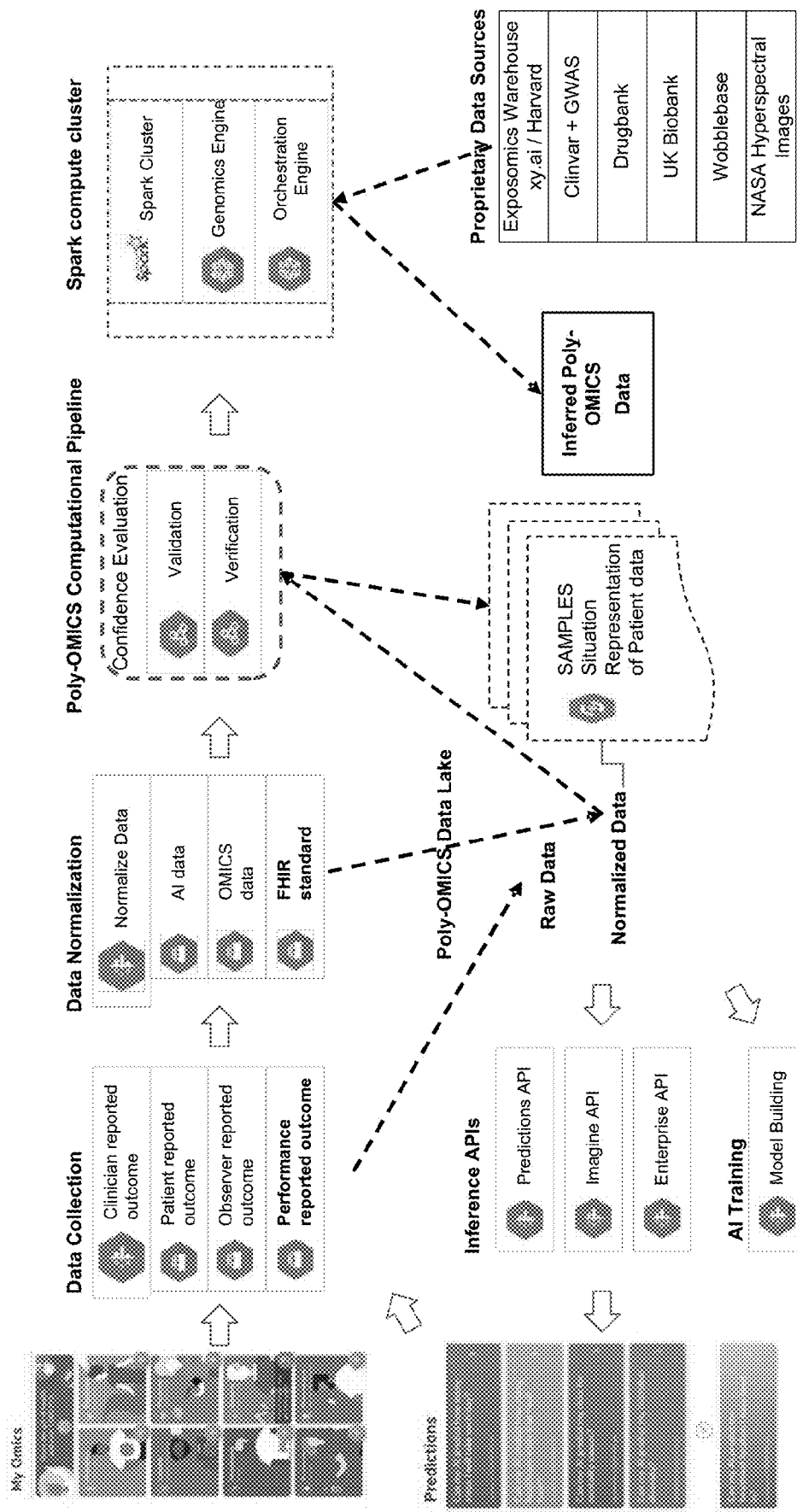
FIG. 21 shows one implementation of a so-called "Polyomics Pipeline."

FIG. 21 shows one implementation of a so-called "Poly-omics Pipeline" 2100.

Artificial Intelligence (AI) Training

Figure 22:
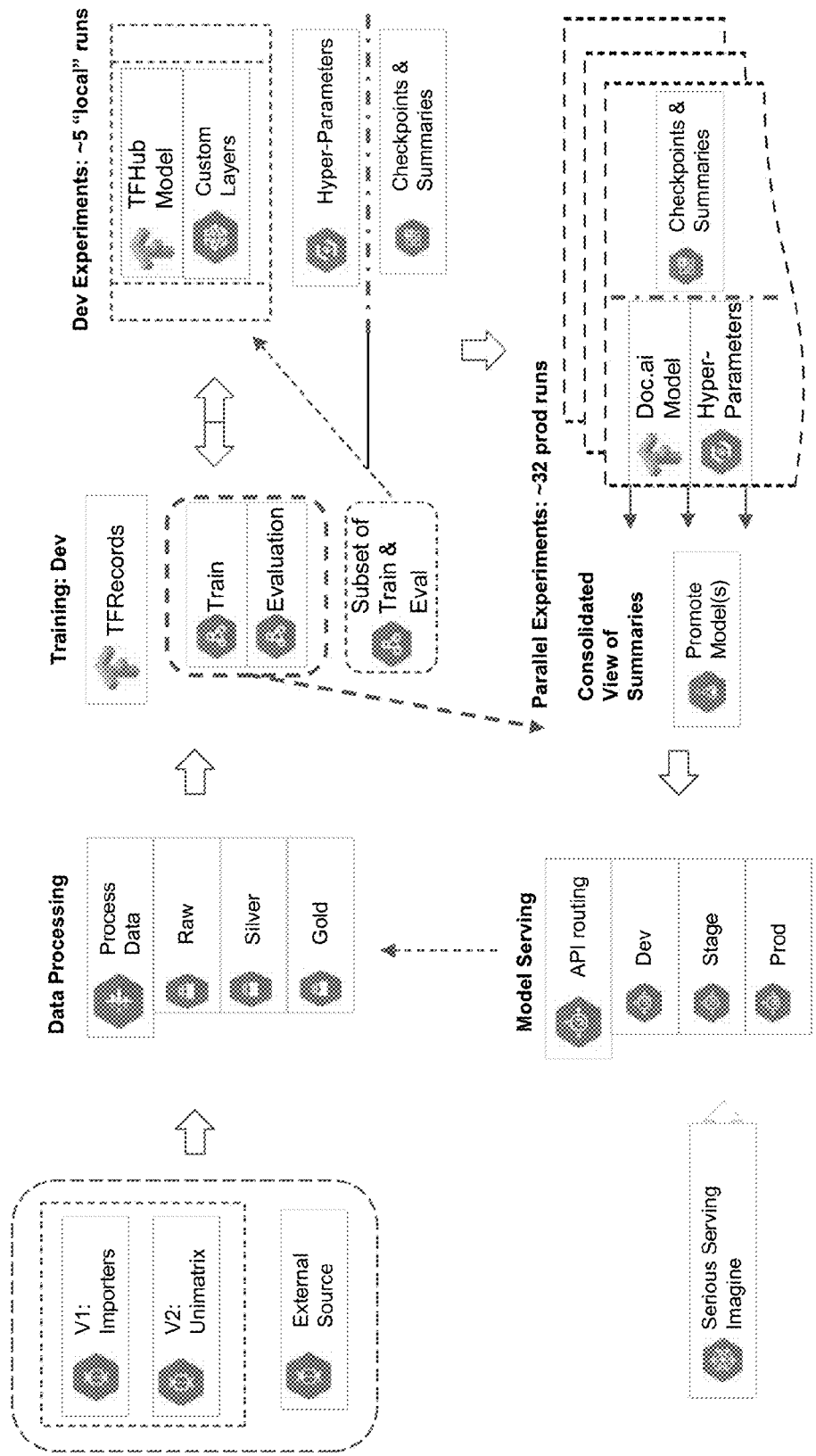
FIG. 22 shows one implementation of a so-called "Artificial Intelligence (AI) Training."

FIG. 22 shows one implementation of a so-called "Artificial Intelligence (AI) Training" 2200.

Particular Implementations

We disclose a deoxyribonucleic acid (DNA) explorer graphic user interface (GUI) for visual exploration of an individual's genetic propensities induced by genetic variants. The GUI comprises a propensity analysis back-end that stores data representing variant-induced propensities of an individual. The GUI comprises a trait and/or disease selection means, which includes a keyword entry window, a natural language query window, a list-based selector, and/or a tree-based selector. The GUI comprises a scrollable DNA display that depicts annotated phenotypes of the individual's chromosomes. The chromosomes are displayed in a consistent order regardless of the selected trait and/or disease. The chromosomes are annotated with feature counts that indicate a number of relevant features on a particular chromosome. At least one chromosome has a plurality of feature count annotations, with the feature count annotations positioned by region across the phenotypes of the at least one chromosome.

The GUI comprises a scrollable single chromosome explorer display that depicts an annotated phenotype with those filtered variants of the individual that are relevant to the selected trait and/or disease and that are displayed at positions within a region of the single chromosome in which they occur.

The GUI further comprises a trait and/or disease-propensity filter that filters, based upon a selected trait and/or disease, the variant-induced propensities of the individual.

The GUI further comprises a nucleotide sequence display that shows a relevant filtered variant nucleotide in context of a nucleotide sequence in which it occurs.

We also disclose a method of visual exploration of an individual's genetic propensities induced by genetic variants. The method includes accessing data representing variant-induced propensities of an individual, depicting annotated phenotypes of the individual's chromosomes, and depicting an annotated phenotype with those filtered variants of the individual that are relevant to the selected trait and/or disease and that are displayed at positions within a region of the single chromosome in which they occur. The chromosomes are displayed in a consistent order regardless of the selected trait and/or disease. The chromosomes are annotated with feature counts that indicate a number of relevant features on a particular chromosome. At least one chromosome has a plurality of feature count annotations, with the feature count annotations positioned by region across the phenotypes of the at least one chromosome.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

One skilled in the art will appreciate that, in other implementations of the streamlined germline browser, the order and arrangement of the user interfaces discussed here and their respective graphic design can change. Also, the susceptibility ratings can take a different form such as numeric scores.

One skilled in the art will appreciate that respective per-disease, cross-chromosomes interfaces 900 can be generated for each of the diseases listed on the susceptibility ratings interface 800 when the users clicks on a corresponding disease.

In this application, implementations that apply to diseases can also apply to traits and vice-versa. For example, the per-disease, cross-chromosomes interface 900 can depict traits. Similarly, the multiple diseases, per-chromosome interface 1200 can depict traits and can be filtered by traits.

Motivation

There is a significant slowdown of direct to consumer genetic testing, and the major companies have already adjusted their forecasts. The market is stagnant for DTC going through the Gartner trough of disillusionment. There are three theories. It can be that those who did not care too much about the privacy aspect have all done it and now we are about to enter the market of the privacy-aware. There are technological means to solve this problem like edge learning, federated learning or hashing. But it can also be that the early adopters have spread the word that what people get from their sequence is not all that actionable. What good does it do to know that you have a variant we cannot treat? Or one that we are not sure about? The third school of thought seems to think that we are our genome but that is not all we are and we need to see the genome as the foundation for the other omics (Eric Topol).

The values that we can deliver today however are quite important.

Birth defects affect one in every 33 babies (about 3% of all babies) born in the United States each year. Birth defects are the leading cause of infant deaths, accounting for 20% of all infant deaths.

More than 6,000 single-gene (Mendelian or monogenic) disorders have been described (World Health Organization, 1997; Online Mendelian Inheritance in Man, 2002), and many more are suspected. These disorders are individually rare but, taken together, are estimated to account for a global birth prevalence of 10 per 1,000 live births (World Health Organization, 1999). Single-gene disorders are classified by mode of inheritance as autosomal recessive or dominant or as X-linked recessive or dominant. For autosomal recessive traits to be expressed, two copies of the mutated gene must be present; thus, if both parents are carriers of the same disease-causing recessive gene, each child has a 25 percent chance of having the disease. See https://www.ncbi.nlm.nih-.gov/books/NBK222082/.

Or more recreationally, we might think of a way where we can do mate selection. The major histocompatibility complex (MHC, HLA in humans) is the genetic component of the immune system. Mammals prefer mates with different genetic MHC code compared to their own. This preference increases the chances of high MHC variety in the offspring, leading to enhanced resilience against a variety of pathogens.

J. Kromer, T. Hummel, D. Pietrowski, A. S. Giani, G. Ehninger, A. H. Schmidt & I. Croy (https://www.nature.com/articles/srep32550) show on a large sample (N=508), with high-resolution typing of HLA class I/II, that HLA dissimilarity correlates with partnership, sexuality and enhances the desire to procreate. We conclude that HLA mediates mate behavior in humans.

Another application could be identification of sperm or egg donors matches, e.g., avoiding diseases that can be done over larger geographical distances.

Clauses

1. A computer-implemented method of efficient tertiary analysis of genomic data, the method including:

splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;

pushing the segments, the indices, and the ledger from the nodes of the distributed storage system to nodes of a distributed, in-memory computing engine;

distributing directives of tertiary analysis job contexts for the genomic data file across the nodes of the distributed, in-memory computing engine;

directly executing the distributed directives on the segments stored on the nodes of the distributed, in-memory computing engine to cause parallel processing of the segments; and aggregating results of the parallel processing across the nodes of the distributed, in-memory computing engine to produce an output.

2. The computer-implemented method of clause 1, further including using a dedicated connector to push the segments, the indices, and the ledger from the nodes of the distributed storage system to the nodes of the distributed, in-memory computing engine.

3. The computer-implemented method of clause 2, wherein the dedicated connector indexes across the nodes of the distributed storage system, and loads the segments onto corresponding ones of the nodes of the distributed, in-memory computing engine.

4. The computer-implemented method of clause 1, further including visually rendering the output according to a pre-configured user interface design.
5. The computer-implemented method of clause 4, further including graphically presenting the visual rendering to users using a frontend application.
6. The computer-implemented method of clause 1, wherein the nodes of the distributed, in-memory computing engine are read-only memories.
7. The computer-implemented method of clause 6, wherein the read-only memories do not require file systems for managing read/write operations.
8. The computer-implemented method of clause 1, wherein the directives of tertiary analysis job contexts are agnostic to changes to the genomic data file.
9. The computer-implemented method of clause 1, further including pre-fetching a reference dataset to the nodes of the distributed, in-memory computing engine, and making the reference dataset available in advance for the parallel processing of the segments.
10. The computer-implemented method of clause 9, wherein the reference dataset has a Parquet format.
11. A system including one or more processors coupled to memory, the memory loaded with computer instructions to perform efficient tertiary analysis of genomic data, the instructions, when executed on the processors, implement actions comprising:
    splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;
    pushing the segments, the indices, and the ledger from the nodes of the distributed storage system to nodes of a distributed, in-memory computing engine;
    distributing directives of tertiary analysis job contexts for the genomic data file across the nodes of the distributed, in-memory computing engine;
    directly executing the distributed directives on the segments stored on the nodes of the distributed, in-memory computing engine to cause parallel processing of the segments; and
    aggregating results of the parallel processing across the nodes of the distributed, in-memory computing engine to produce an output.
12. The system of clause 11, wherein the nodes of the distributed, in-memory computing engine are read-only memories that do not require file systems for managing read/write operations.
13. The system of clause 11, wherein the directives of tertiary analysis job contexts are agnostic to changes to the genomic data file.
14. The system of clause 11, further implementing actions comprising pre-fetching a reference dataset to the nodes of the distributed, in-memory computing engine, and making the reference dataset available in advance for the parallel processing of the segments.
15. A non-transitory computer readable storage medium impressed with computer program instructions to perform efficient tertiary analysis of genomic data, the instructions, when executed on a processor, implement a method comprising:
    splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;
    pushing the segments, the indices, and the ledger from the nodes of the distributed storage system to nodes of a distributed, in-memory computing engine;
    distributing directives of tertiary analysis job contexts for the genomic data file across the nodes of the distributed, in-memory computing engine;
    directly executing the distributed directives on the segments stored on the nodes of the distributed, in-memory computing engine to cause parallel processing of the segments; and
    aggregating results of the parallel processing across the nodes of the distributed, in-memory computing engine to produce an output.
16. The non-transitory computer readable storage medium of clause 15, wherein the nodes of the distributed, in-memory computing engine are read-only memories that do not require file systems for managing read/write operations.
17. The non-transitory computer readable storage medium of clause 15, wherein the directives of tertiary analysis job contexts are agnostic to changes to the genomic data file.
18. The non-transitory computer readable storage medium of clause 15, implementing the method further comprising pre-fetching a reference dataset to the nodes of the distributed, in-memory computing engine, and making the reference dataset available in advance for the parallel processing of the segments.
19. A computer-implemented method of efficient tertiary analysis of genomic data, the method including:
    splitting a genomic data file into a plurality of segments, and storing segments in the plurality of segments across nodes of a distributed storage system;
    pushing the segments from the nodes of the distributed storage system to nodes of a distributed, in-memory computing engine;
    distributing directives of tertiary analysis job contexts for the genomic data file across the nodes of the distributed, in-memory computing engine;
    directly executing the distributed directives on the segments stored on the nodes of the distributed, in-memory computing engine to cause parallel processing of the segments; and
    aggregating results of the parallel processing across the nodes of the distributed, in-memory computing engine to produce an output.

One or more implementations of the technology disclosed, or elements thereof can be implemented in the form of a computer product including a non-transitory computer readable storage medium with computer usable program code for performing the method steps indicated. Furthermore, one or more implementations of the technology disclosed, or elements thereof can be implemented in the form of an apparatus including a memory and at least one processor that is coupled to the memory and operative to perform exemplary method steps. Yet further, in another aspect, one or more implementations of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

Computer System

Figure 23:
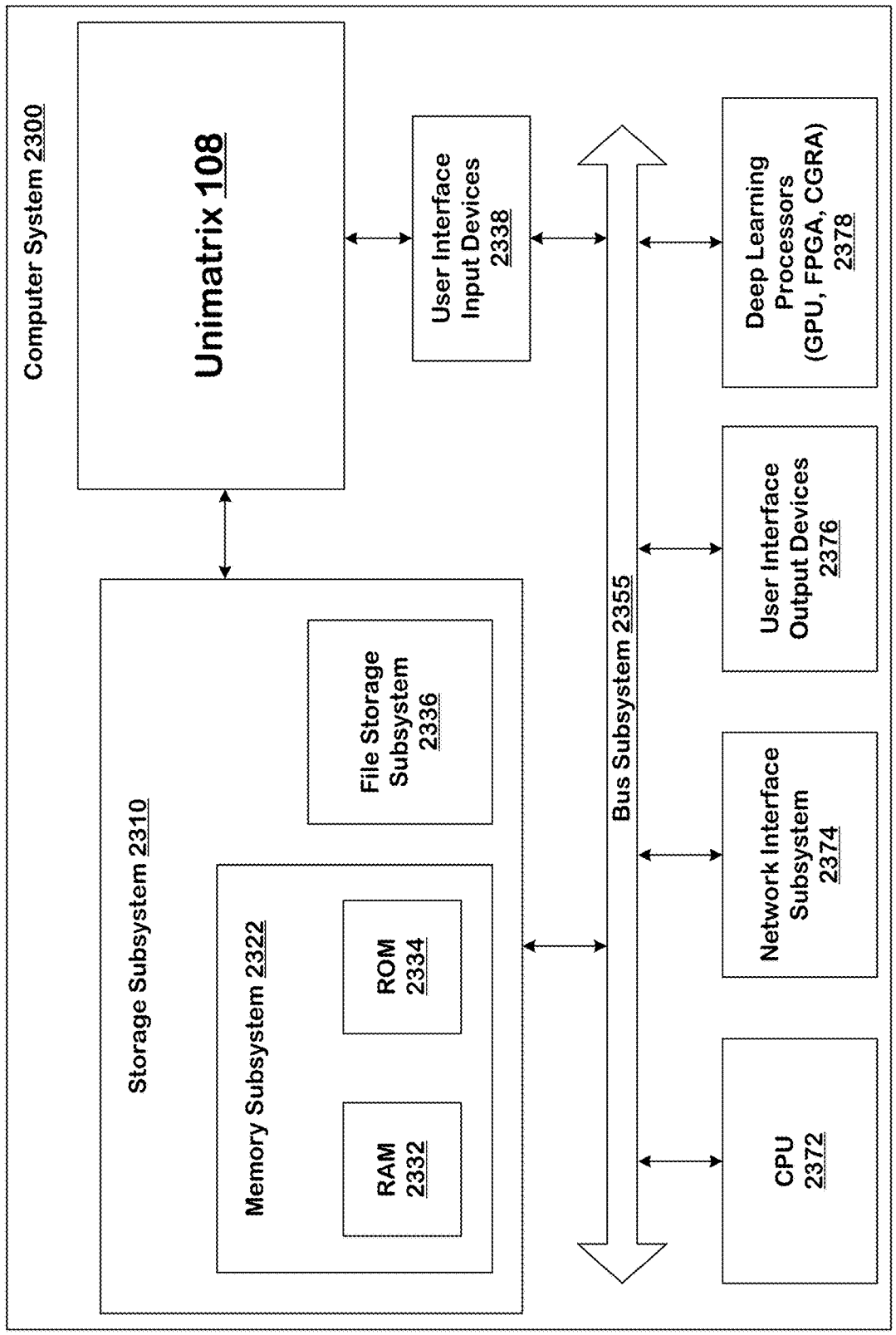
FIG. 23 is a computer system that can be used to implement the technology disclosed.

FIG. 23 is a computer system 2300 that can be used to implement the technology disclosed. Computer system 2300 includes at least one central processing unit (CPU) 2372 that communicates with a number of peripheral devices via bus subsystem 2355. These peripheral devices can include a storage subsystem 2310 including, for example, memory devices and a file storage subsystem 2336, user interface input devices 2338, user interface output devices 2376, and a network interface subsystem 2374. The input and output devices allow user interaction with computer system 2300. Network interface subsystem 2374 provides an interface to outside networks, including an interface to corresponding interface devices in other computer systems.

In one implementation, Unimatrix 108 is communicably linked to the storage subsystem 2310 and the user interface input devices 2338.

User interface input devices 2338 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2300.

User interface output devices 2376 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2300 to the user or to another machine or computer system.

Storage subsystem 2310 stores programming and data constructs that provide the functionality of some or all of the modules and methods described herein. These software modules are generally executed by deep learning processors 2378.

Deep learning processors 2378 can be graphics processing units (GPUs), field-programmable gate arrays (FPGAs), application-specific integrated circuits (ASICs), and/or coarse-grained reconfigurable architectures (CGRAs). Deep learning processors 2378 can be hosted by a deep learning cloud platform such as Google Cloud Platform™, Xilinx™, and Cirrascale™. Examples of deep learning processors 2378 include Google's Tensor Processing Unit (TPU)™, rackmount solutions like GX4 Rackmount Series™, GX23 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™ NVIDIA's DRIVE PX™, NVIDIA's JETSON TX1/TX2 MODULE™, Intel's Nirvana™ Movidius VPU™, Fujitsu DPI™, ARM's DynamicIQ™, IBM TrueNorth™, and others.

Memory subsystem 2322 used in the storage subsystem 2310 can include a number of memories including a main random access memory (RAM) 2332 for storage of instructions and data during program execution and a read only memory (ROM) 2334 in which fixed instructions are stored. A file storage subsystem 2336 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2336 in the storage subsystem 2310, or in other machines accessible by the processor.

Bus subsystem 2355 provides a mechanism for letting the various components and subsystems of computer system 2300 communicate with each other as intended. Although bus subsystem 2355 is shown schematically as a single bus, alternative implementations of the bus subsystem can use multiple busses.

Computer system 2300 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2300 depicted in FIG. 23 is intended only as a specific example for purposes of illustrating the preferred implementations of the present invention. Many other configurations of computer system 2300 are possible having more or less components than the computer system depicted in FIG. 23.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A computer-implemented method of efficient tertiary analysis of genomic data, the method including:
   splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;
   pushing the segments, the indices, and the ledger from the nodes of the distributed storage system to nodes of a distributed, in-memory computing engine;
   distributing directives of tertiary analysis job contexts for the genomic data file across the nodes of the distributed, in-memory computing engine;
   directly executing the distributed directives on the segments stored on the nodes of the distributed, in-memory computing engine to cause parallel processing of the segments; and
   aggregating results of the parallel processing across the nodes of the distributed, in-memory computing engine to produce an output.

2. The computer-implemented method of claim 1, further including using a dedicated connector to push the segments, the indices, and the ledger from the nodes of the distributed storage system to the nodes of the distributed, in-memory computing engine.

3. The computer-implemented method of claim 2, wherein the dedicated connector indexes across the nodes of the distributed storage system, and loads the segments onto corresponding ones of the nodes of the distributed, in-memory computing engine.

4. The computer-implemented method of claim 1, wherein the read-only memories do not require file systems for managing read/write operations.

5. The computer-implemented method of claim 4, wherein the directives of tertiary analysis job contexts are agnostic to changes to the genomic data file.

6. The computer-implemented method of claim 1, wherein the directives of tertiary analysis job contexts are agnostic to changes to the genomic data file.

7. The computer-implemented method of claim 1, further including pre-fetching a reference dataset to the nodes of the distributed, in-memory computing engine, and making the reference dataset available in advance for the parallel processing of the segments.

8. The computer-implemented method of claim 7, wherein the reference dataset has a Parquet format.

9. A system including one or more processors coupled to memory, the memory loaded with computer instructions to perform efficient tertiary analysis of genomic data, the instructions, when executed on the processors, implement actions comprising:
  splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;
  pushing the segments, the indices, and the ledger from the nodes of the distributed storage system to nodes of a distributed, in-memory computing engine;
  distributing directives of tertiary analysis job contexts for the genomic data file across the nodes of the distributed, in-memory computing engine;
  directly executing the distributed directives on the segments stored on the nodes of the distributed, in-memory computing engine to cause parallel processing of the segments; and
  aggregating results of the parallel processing across the nodes of the distributed, in-memory computing engine to produce an output.

10. The system of claim 9, wherein the nodes of the distributed, in-memory computing engine are read-only memories that do not require file systems for managing read/write operations.

11. The system of claim 9, wherein the directives of tertiary analysis job contexts are agnostic to changes to the genomic data file.

12. The system of claim 9, further implementing actions comprising pre-fetching a reference dataset to the nodes of the distributed, in-memory computing engine, and making the reference dataset available in advance for the parallel processing of the segments.

13. A non-transitory computer readable storage medium impressed with computer program instructions to perform efficient tertiary analysis of genomic data, the instructions, when executed on a processor, implement a method comprising:
  splitting a genomic data file into a plurality of segments, and storing segments in the plurality of segments across nodes of a distributed storage system, the distributed storage system indexing entries in the genomic data file using one or more indices, and generating a ledger that maps ranges of the indices to corresponding ones of the nodes on which the entries are stored;
  pushing the segments, the indices, and the ledger from the nodes of the distributed storage system to nodes of a distributed, in-memory computing engine;
  distributing directives of tertiary analysis job contexts for the genomic data file across the nodes of the distributed, in-memory computing engine;
  directly executing the distributed directives on the segments stored on the nodes of the distributed, in-memory computing engine to cause parallel processing of the segments; and
  aggregating results of the parallel processing across the nodes of the distributed, in-memory computing engine to produce an output.

14. The non-transitory computer readable storage medium of claim 13, wherein the nodes of the distributed, in-memory computing engine are read-only memories that do not require file systems for managing read/write operations.

15. The non-transitory computer readable storage medium of claim 13, wherein the directives of tertiary analysis job contexts are agnostic to changes to the genomic data file.

* * * * *